United States Patent [19]

Faulds

[11] Patent Number: 5,240,706
[45] Date of Patent: Aug. 31, 1993

[54] **INTRANASAL ADMINISTRATION OF *MYCOPLASMA HYOPNEUMONIAE* ANTIGEN**

[75] Inventor: Daryl Faulds, Millbrae, Calif.

[73] Assignee: ML Technology Ventures, L.P., New York, N.Y.

[21] Appl. No.: 334,586

[22] Filed: Apr. 7, 1989

[51] Int. Cl.$^5$ .................. A61K 39/02; C12P 21/06
[52] U.S. Cl. ........................................ 424/92; 424/88; 435/69.1; 435/69.3; 435/71.1; 435/172.1; 435/172.3; 435/870; 935/12; 935/31; 935/65; 935/81; 530/350; 530/806; 530/820; 530/821
[58] Field of Search ............... 424/92, 88; 435/69.1, 435/69.3, 71.1, 172.1, 172.3, 870; 935/12, 31, 65, 81; 530/350, 806, 820, 821

[56] References Cited

U.S. PATENT DOCUMENTS

| | | | |
|---|---|---|---|
| 4,894,332 | 1/1990 | Schaller et al. | 424/92 |
| 4,985,243 | 1/1991 | Faulds et al. | 424/88 |

FOREIGN PATENT DOCUMENTS

| | | |
|---|---|---|
| 0196215 | 10/1986 | European Pat. Off. . |
| 0283840 | 9/1988 | European Pat. Off. . |
| WO88/00977 | 2/1988 | PCT Int'l Appl. . |

OTHER PUBLICATIONS

Wise et al., *Chemical Abstracts*, vol. 107, Ref. No. 196101d, 1987.
Ross et al., *Amer. J. Vet. Res.* vol. 45, No. 10, pp. 1899-1905, 1984.
Schaller et al., *Chemical Abstracts*, vol. 106, Reference #143977s, 1987.
Young et al., *Chemical Abstracts*, vol. 106, Reference #212183y, 1987.
Klinkert et al., *Chemical Abstracts*, vol. 103, Reference #103070x, 1985.
Tajuna et al., *Biological Abstracts*, vol. 79, Reference #31582, 1984.
Jacobs et al., *Chemical Abstracts*, vol. 108, Reference #148536y, 1988.

*Primary Examiner*—Michael G. Wityshyn
*Assistant Examiner*—Abdel A. Mohamed
*Attorney, Agent, or Firm*—Elliot M. Olstein; Raymond J. Lillie

[57] ABSTRACT

A method for protecting an animal, in particular swine, against mycoplasma pneumonia by administering intranasally to the animal a vaccine containing one or more proteins which elicits an antibody which recognizes a *Mycoplasma hyopneumoniae* antigen which lacks immunosuppressive activity. A particularly preferred intranasal vaccine includes the 74.5 kDa antigen of *Mycoplasma hyopneumoniae*. The 74.5 kDa antigen may be of recombinant origin.

10 Claims, 20 Drawing Sheets

LEGEND

H Hind III
R1 EcoRI
X XhoI
L Hind III-PstI-EcoRI
□ pUC9
■ MYCOPLASMA, 41 KDa
▨ MYCOPLASMA, UNKOWN

LEGEND

H Hind III
X XhoI
□ pWHA148
■ MYCOPLASMA

FIG. 6A

```
  1
met ala lys glu ile ile leu gly ile asp leu gly thr thr asn
ATC GCA AAA GAA ATC ATT TTA CGA ATC GAC CTY GGA ACA ACA AAC 30                              30
ser val val ala ile ile glu asn gln lys pro val val leu glu
TCA GTT GTT GCA ATT ATT GAA AAT CAA AAA CCT GTC GTT CTC GAA 40
asn pro asn gly lys arg thr thr pro ser val val ala phe lys
AAT CCC AAC GGA AAA AGA ACA ACT CCA TCC GTT GTC GCT TTT AAA 50                              60
asn asn glu glu ile val gly asp ala ala lys arg gln leu glu
AAC AAT GAA GAA ATT GTC GGG GAT GCA GCT AAA AGA CAA CTT GAA 70
thr asn pro glu ala ile ala ser ile lys arg leu met gly thr
ACT AAC CCA GAA GCA ATC GCT TCA ATT AAA AGA TTA ATG GGA ACT 80                              90
asp lys thr val arg ala asn glu arg asp tyr ile pro glu glu
GAT AAA ACA GTT CGT GCA AAT GAA AGA GAT TAT ATT CCT GAA GAA 100
ile ser ala lys ile leu ala tyr leu lys glu tyr ala glu lys
ATC TCG GCA AAA ATT CTT GCT TAT TTA AAA GAA TAT GCT GAG AAA
```

MATCH WITH FIG. 6B

FIG. 6B

MATCH WITH FIG. 6A

```
                            110                                     120
lys ile gly his lys val thr lys ala val ile thr val pro ala
AAG ATT GGT CAT AAA GTA ACA AAA GCA GTA ATT ACA GTA CCT GCT 130
thr phe asp asn ala gln arg glu ala thr lys asn ala gly lys
TAT TTT GAC AAT GCC CAA CGT GAG GCA ACA AAA AAT GCC GGA AAC 140                                     150
ile ala gly leu gln val glu arg ile ile asn glu pro thr ala
ATC GCT GGA TTA CAA GTA GAA AGA ATT ATA AAT GAA CCA ACA GCG 160
ala ala leu ala phe gly leu asp lys thr glu lys glu met lys
GCC GCA CTT GCT TTT GGC CTT GAT AAA ACT GAA AAA GAA ATG AAA 170                                     180
val leu val tyr asp leu gly gly gly thr phe asp val ser val
GTT CTT GTC TAT GAC TTA GGT GGG GGA ACT TTT GAT GTC TCA GTT 190
leu glu leu ser gly gly thr phe glu val leu ser thr ser gly
TTA GAA TTA TCC GGT GGA ACC TTC GAA GTT TTA TCA ACA ACT GGA 200                                     210
asp his leu gly gly asp asp trp asp asp glu ile val asp
GAT AAT CAT TTA GGT GGG GAT GAC TGG GAT GAT GAA ATT GTA AAT
```

MATCH WITH FIG. 6C

FIG. 6C

MATCH WITH FIG. 6B

```
                                          220
trp leu val lys ile lys glu val tyr asp phe asp pro lys
TGA CTT GTT AAA ATC AAA GAA GTA TAT GAT TTT GAT CCA AAA
                                                      240
            230                                       lys
ser asp lys met ala leu thr arg leu lys glu glu ala glu
AGT GAT AAA ATG GCG CTT ACA AGA CTT AAA GAA GAG GCT GAA AAA
                              250
thr lys ile asp leu ser asp gln ser val ser thr val ser leu
ACC AAA ATT AAT CTT TCA AAT CAA AGT GTT TCT ACA GTT TCT CTA
              260                                     270
pro phe leu gly met gly lys asp gly pro ile asp val glu leu
CCA TTT TTA GGA ATG GGC AAA AAC GGG CCG ATT AAC GTT GAA CTT
                              280
glu leu lys arg ser glu phe glu lys met thr ala his leu ile
GAA CTT AAA AGA TCA GAA TTT GAA AAA ATG ACT GCC CAT TTA ATC
              290                                     300
                                                      lys
asp arg thr arg lys pro ile val asp ala leu lys gln ala lys
GAT AGA ACT CGC AAA CCA ATT GTT GAT GCT CTA AAA CAA GCA AAA
                              310
ile glu ala ser asp leu asp glu val leu leu val gly gly ser
ATT GAG GCT TCA GAT CTT GAT GAA GTT CTC CTT GTA GGT GGA TCA
```

MATCH WITH FIG. 6D

MATCH WITH FIG. 6C

FIG. 6D

```
                                    330
thr arg met pro ala val gln ser met ile glu his thr leu asp
ACA AGA ATG CCA GCT GTT CAG TCA ATG ATT GAG CAT ACT TTA AAT 340
lys lys pro asp arg ser ile asp pro glu val val ala ile
AAA AAG CCA AAT CGT TCA ATT AAT CCT GAT GAG GTA GTC GCA ATT 350                                         360
gly ala ala ile gln gly val leu ala gly ile ser asp
CGT GCT GCA ATT CAA GGG GGG GTT CTA GCT GGA GAG ATC AGT GAT 370
val leu leu asp val thr pro leu thr leu gly ile glu thr
GTT CTA CTT TTA GAT GTT ACT CCT TTA ACT TTA GGA ATT GAA ACT 380                                 390
leu gly gly ile ala thr pro leu ile pro arg asp thr ile
TTA GGT GGA ATT GCA ACA CCT TTG ATT CCA AGA AAT ACA ATT 400
pro val thr lys ser gln ile phe ser thr ala glu asp asn gln
CCG GTA ACA AAA TCA CAA ATT TTC TCA ACA GCT GAG GAT AAT CAA 420
thr glu val thr ile ser val val gln gly glu arg gln leu ala
ACC GAA GTA ACA ATT TCT GTT GTC CAA GGT GAA CGT CAA CTT GCA
```

MATCH WITH FIG. 6E

FIG. 6E

MATCH WITH FIG. 6D

```
                                    430
ala asp asn lys met leu gly arg phe asn leu ser gly ile glu
GCG GAT AAT AAA ATG TTA GGT CGC TTT AAT TTA TCA GGA ATT GAA 450
              440                                       ser ile
ala ala pro arg gly leu pro gln ile glu val ser phe
GCT GCT CCA CGA GGT CTT CCC CAG ATT GAA GTT AGT TTT TCA ATT 460
asp val asn gly ile thr thr val ser ala lys asp lys lys thr
GAT GTC AAC GGG ATT ACA ACG GTT TCA GCA AAA GAT AAA AAA ACC 470                                             480
gly lys glu gln thr ile lys asn thr ser thr leu ser
GGC AAA GAA CAA ATT ACA ATT AAA AAT ACT TCA ACT TTA TCA 490
glu glu ile asn lys met ile gln ala glu glu asn arg
GAA GAA ATT AAT AAG ATG ATT CAG GAA GCC GAA GAA AAT CGT 500                                     510
glu ala asp lys leu lys lys asp lys ile glu thr thr val arg
GAA GCT GAT AAA CTT AAA AAA GAC AAA ATC GAG ACA ACA GTT CGT 520
ala glu gly leu ile asn gln leu glu lys ser ile thr asp gln
GCC GAA GGG CTT ATT AAT CAA CTT GAG AAA TCA ATA ACT GAT CAA
```

MATCH WITH FIG. 6F

MATCH WITH FIG. 6E

FIG. 6F

```
                         530                               540
gly glu lys ile asp pro lys gln lys glu leu leu glu lys gln
GGT GAA AAA ATT GAT CCA AAA CAA AAA GAA TTA CTT GAA AAA CAA 550
ile gln glu leu lys asp leu leu lys glu asp lys thr asp glu
ATT CAA GAA TTA AAA GAT CTT CTA AAA GAA GAT AAA ACT GAC GAA 560                                               570
leu lys leu lys leu asp gln ile glu ala ala ala gln ser phe
TTA AAA TTA AAA TTA GAC CAA ATT GAA GCA GCT GCC CAA TCT TTT 580
ala gln ala thr ala gln gln ala asn thr ser glu ser asp pro
GCG CAG GCA ACC GCG CAG CAA AAT ACA TCT GAA TCT GAT CCA 590                                               600
lys ala asp asp ser asn thr ile asp ala glu ile lys gln asp
AAA GCT GAT GAT TCA AAC ACA ATT GAT GCT GAA ATC AAG CAG GAT
```

FIG. 7

```
  1                                        10
met thr met ile thr asn ser ser ser val pr atg acc atg att acg aat tcg agc tcg gta ccc
tac tgg tac taa tgc tta agc tcg agc cat ggg cc
```

```
|---------------------------------------------->
 pUC18          |                  |
              EcoR1              KpnI
```

```
                                20
asp pro leu glu ser thr cys arg his ala SER SER gat cct cta gag tcg acc tgc agg cat gca AGC TCC
cta gga gat ctc agc tgg acg tcc gta cgt tcg aGG
-----------------------------------------| |->
                                 |
                               SphI
```

```
                    30
ARG PRO GLY ALA ARG ASP LEU GLY PRO ASP ARG CYS

AGG CCT GGC GCG CGA GAT CTC GGG CCC GAT CGA TGC
TCC GGA CCG CGC GCT CTA GAG CCC GGG CTA GCT ACG

---------------------------------------------->
 pWHA148 addition
                 40
ARG GLY ASP ILE ALA ARG GLY SER leu ala CGC GGC GAT ATC GCT CGA GGA agc ttg gca
GCG CCG CTA TAG CGA GCT CCT TCG Aac cgt -------------------------------|  |----->
                    |       |     pUC18
                  XhoI    HindIII
```

Position of pUC18 conserved sequences, addition endpoints and predicted partial amino acid sequence of the beta-galactosidase fusion protein produced in pWHA148. A portion of the nucleotide sequence of pUC18 is designated by lower case letters; the nucleotide sequence of the pWHA148 synthetic oligonucleotide addition is designated by upper case letters. Numbers refer to the order of the expected amino acid sequence.

LEGEND
AS AsuII
C ClaI
H HindIII
L HindIII-PstI
R EcoRI
■ pUC9
☐ MYCOPLASMA
■ trpT176

FIG. 14A

```
      1
met asp lys phe arg tyr val lys pro gly gln ile met ala lys
ATG GAC AAA TTT CGC TAT GTA AAG CCT GGA CAA ATT ATG GCA AAA 30
asp glu met ile arg phe leu asp ile asp gly asn leu leu
GAT GAA ATG ATT CGC TTT CTT GAT ATT GAT GGT AAT CTT TTA 20
ser ser thr val phe gly pro ile asp glu thr asn asp ile arg
TCT TCA ACT GTT TTT GGA CCA ATC GAC GAA ACA AAT GAT ATT CGC 50                                             60
leu ser lys gln glu ile lys lys ala tyr glu phe met val leu
TTA TCA AAA CAG GAA ATC AAA AAA GCT TAT GAA TTT ATG GTT TTA ser arg gln asp thr tyr met thr gln leu gln arg gln gly
TCT CGC CAA CAA GAT ACG TAT ATG ACA CAA CTA CAG CGA CAA GGT 80                                             90
arg met leu thr phe ala pro asn phe gly glu glu ala leu gln
AGA ATG TTG ACT TTT GCC CCT AAC TTT GGT GAA GAA GCT CTT CAA 100
val ala ser gly met ala leu thr lys asp asp trp phe val pro
GTA GCC TCA GGG ATG GCG CTA ACA AAA GAT GAC TGA TTT GTC CCA
```

MATCH WITH FIG. 14B

FIG. 14B

MATCH WITH FIG. 14A

```
                    110                                   120
ala phe arg ser asn ala thr met leu tyr leu gly val pro met
GCT TTT CGT TCA AAT GCA ACA ATG TTA TAT CTT GGC GTG CCA ATG 130                                150
ile leu gln met gln tyr trp asn gly ser glu lys gly asn val
ATC TTG CAA ATG CAA TAT TGA AAT GGT AGC GAA AAA GGT AAT GTA 140
ile pro glu asn val leu pro ile asn ile pro ile gly
ATT CCC GAA AAT GTT TTA CCT ATT AAC ATT CCC ATC GGA 160
thr gln phe ser his ala ala gly ile ala tyr ala ala lys leu
ACG CAG TTT TCC CAT GCT GCC GGA ATT GCT TAT GCA GCA AAA CTA 170                                          180
thr gly lys lys val ile ser met phe ile gly asn gly gly
ACA GGT AAA AAA GTT TCA ATG AGT TTT ATT GGA AAC GGG GGA 190
thr ala glu gly glu phe tyr glu ala leu asn ile ala ser ile
ACT GCC GAA GGC GAG TTT TAC GAA GCG CTA AAT ATT GCA AGT ATT 200                                          210
trp lys trp pro val val phe cys val asn asn asn gln trp ala
TGA AAA TGA CCA GTT GTT TTT TGC GTA AAC AAC AAC CAA TGA GCA
```

MATCH WITH FIG. 14C

FIG. 14C

MATCH WITH FIG. 14B

```
ile ser thr pro asn lys tyr glu asn  220 ala ser thr ile ala
                                    gly
ATT TCA ACC CCA AAC AAA TAT GAA AAC GGA GCC TCA ACA ATT GCT ala lys ala met  230 ala gly ile pro gly ile arg val asp  240
                ala                                      gly
GCA AAA GCA ATG GCA GCA GGA ATT CCT GGA ATT CGT GTA GAC GGA asn asp leu leu ala ser tyr glu val  250 lys glu ala val asp
                                    ile
AAT GAC CTT TTA GCT TCT TAT GAA GTA ATC AAG GAA GCT GTT GAT tyr ala arg ser  260 asn gly pro val leu val glu phe val  270
                gly                                      thr
TAT GCT CGT TCT GGA AAC GGT CCT GTT CTT GTT GAG TTT GTA ACT trp arg gln gly val his thr ser ser  280 asn pro arg ile tyr
                                    asp
TGA CGT CAA GGT GTT CAT ACC TCT TCT GAT AAT CCA CGA ATT TAT arg thr val glu glu glu lys glu his glu lys trp glu pro  300
                                                        met
CGT ACT GTT GAA GAG GAA AAA GAA CAC GAA AAA TGA GAA CCA ATG his arg ile glu lys tyr met phe asp  310 gly phe ile asp ser
                                    arg
CAC CGG ATT GAA AAA TAT ATG TTT GAC CGC GGA TTT ATT GAT TCT
```

MATCH WITH FIG. 14D

FIG. 14D

MATCH WITH FIG. 14C

```
                    320                             330
thr asp ser gln pro asn leu arg trp ser ala cys asp cys gln
ACC GAT AGT CAA CCT AAT TTG AGA TGA AGC GCT TGC GAT TGT CAA 340
arg asn leu trp lys ile ser cys trp ala trp val asn asn trp
AGA AAC TTA TGA AAA ATC TCT TGT TGG GCT TGA GTC AAC AAT TGA 350                                        360
trp asn phe arg ser tyr leu gln gly phe thr thr arg thr trp
TGA AAT TTT CGA TCA TAC CTA CAA GGT TTT ACC ACC AGA ACT TGA 370
arg thr lys thr arg ser ala trp ile phe oc
AGA ACA AAA ACA AGA AGC GCT TGA ATT TTT TAA
```

Translated Mol. Weight = 42357.94

LEGEND

L Pst-HindIII. AND OTHERS
C/B ClaI-50bp-BglII
C ClaI

LEGEND

As AsuII
B BglII
C ClaI
C/B ClaI.BglII
CLOSE TOGETHER
H HindIII
☐ M13mp18
▨ pMYC031

FIG. 17

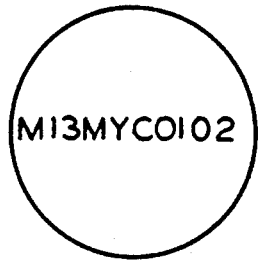

T4 (BOEHRINGER MANN-HEIM) PHOSPHORYLATED MUTANT OLIGONUCLEOTIDE

SINGLE STRAND DNA TEMPLATE

↓ ANNEAL

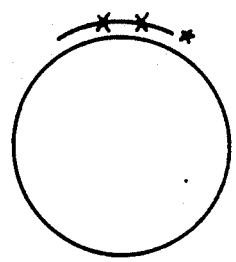

EXTEND AND LIGATE WITH KLENOW DNA POLYMERASE, T4 LIGASE (AMERSHAM), dNTP'S, AND dCTPαS

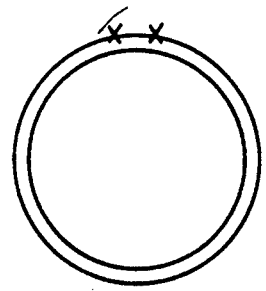

DIGEST WITH (AMERSHAM), (NICKS UNPROTECTED STRAND)

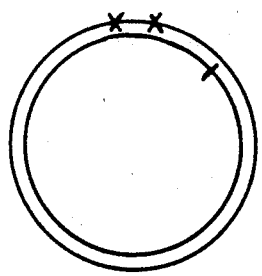

PARTIAL EXONUCLEASE III (AMERSHAM) DIGEST

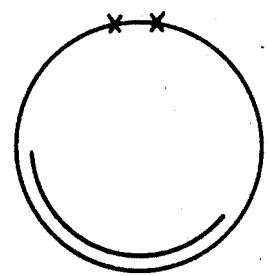

EXTEND AND LIGATE WITH DNA POLYMERASE I, T4 DNA LIGASE (AMERSHAM), AND dNTP'S

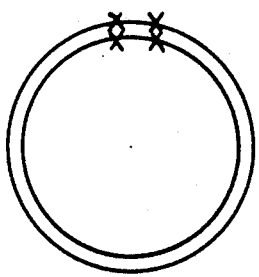

TRANSFORM INTO E.coli STRAIN JM103

LEGEND
As AsuII
B BgIII
C ClaI
C/B ClaI.BgIII CLOSE TOGETHER
H HindIII
☐ M13mp18
▨ pMYCO31

LEGEND
As AsuII
H HindIII
P PstI
Pf PflmI
R EcoRI
T ThaI
▨ = M13mp18
▨ = 74.5 CODING REGION
▨ = MYCOPLASMA DNA
▨ = trpT 176
NUMBERS REFER TO KILOBASE PAIRS

INTRANASAL ADMINISTRATION OF *MYCOPLASMA HYOPNEUMONIAE* ANTIGEN

This invention relates to *Mycoplasma hyopneumoniae* (*M. hyopneumoniae*), and more particularly to *Mycoplasma hyopneumoniae* antigens. More particularly, this invention relates to an intranasally-administered vaccine for protecting against mycoplasmal pneumonia, and in particular mycoplasmal pneumonia of swine.

The disease caused by *Mycoplasma hyopneumoniae* (in particular in swine) occurs throughout the world and is a disease associated with the loss of swine. The disease generally results in inefficient, stunted and sickly animals, and affected swine are often prone to secondary infection by opportunistic microorganisms.

Kristensen. et al., in *Am. J. Vet. Res.*, Vol. 42 (1981), page 784, found no protection of swine against mycoplasmal pneumonia after injection with heat inactivated cells of *Mycoplasma hyopneumoniae*. Etheridge, et al., *Res. Vet Sci*, Vol. 33 (1982) page 188, found incomplete protection against lung colonization by Mycoplasma when a live vaccine was given intravenously, subcutaneously, and intraperitoneally.

Ross. et al., *Am. J. Vet. Res.*, Vol. 45 (1984) page 1899, disclosed that the use of *Mycoplasma hyopneumoniae* extracts prepared by a freeze thaw procedure provided only variable protection, and, in some instances, enhanced lesion development. This article also claimed that injection of such agent into swine gave some level of protection against an intratracheal challenge exposure consisting of 4 ml of supernatant from a 10% suspension of pneumonic lung containing straim VPP-11 combined with 1 ml of a 24 hour culture of 15 to 20 passages of the same strain.

Copending U.S. patent application Ser. No. 030,130, filed Mar. 26, 1987, discloses a vaccine for protection against mycoplasmal pneumonia which comprises one or more proteins which produce an antibody which recognizes a *Mycoplasma hyopneumoniae* antigen which lacks immunosuppressive activity. The vaccine includes the protein in an amount effective for protection against mycoplasmal pneumonia, and is essentially free of *Mycoplasma hyopneumoniae* antigens which have immunosuppressive activity.

Copending U.S. patent application Ser. No. 213.248, filed Jun. 29. 1988, discloses the preparation of recombinant *Mycoplasma hyopneumoniae* antigens, and the use of such recombinant antigens in a vaccine against mycoplasmal pneumonia.

In accordance with an aspect of the present invention, there is provided a method for protecting an animal against mycoplasmal pneumonia which comprises administering intranasally to the animal a vaccine comprising one or more proteins which elicit an antibody which recognizes a *Mycoplasma hyopneumoniae* antigen which lacks immunosuppressive activity, said vaccine including said one or more proteins in an amount effective for protection against mycoplasmal pneumonia said vaccine being essentially free of *Mycoplasma hyopneumoniae* antigens which have immunosuppressive activity.

Applicant has found that when a vaccine containing at least one *Mycoplasma hyopneumoniae* antigen is administered intranasally, that such vaccine provides more effective protection against mycoplasmal pneumonia, in particular mycoplasmal pneumonia in swine, than a vaccine administered by systemic methods (e.g., intramuscularly, etc.).

The term "protection" when used with respect to the intranasally administered vaccine for mycoplasmal pneumonia described herein means that the vaccine prevents mycoplasmal pneumonia and/or reduces the severity of mycoplasmal pneumonia.

The one or more proteins may elicit an antibody which recognizes a *Mycoplasma hyopneumoniae* antigen which has a molecular weight of at least 10 kDa and no greater than 350 kDa. The one or more proteins may elicit an antibody which recognizes at least one of the 22.5 kDa, 34 kDa, 36 kDa, 41 kDa, 44 kDa, 48 kDa, 52 kDa, 64 kDa, 74.5 kDa, 79 kDa, 88.5 kDa, 96.5 kDa, or 121 kDa *M. hyopneumoniae* antigens. The one or more proteins may be the 22.5 kDa, 34 kDa, 36 kDa, 41 kDa, 44 kDa, 48 kDa, 52 kDa, 64 kDa, 74.5 kDa, 79 kDa, 88.5 kDa, 96.5 kDa or 121 kDa *M. hyopneumoniae* antigen or fragment or derivative thereof. The molecular weights for characterizing the antigens are obtained by discontinuous polyacrylamide gel electrophoresis using the SDS buffer system described by Laemmli, *Nature*, Vol. 227, pgs. 680–85 (1970). In a particularly preferred embodiment, the one or more proteins is the 74.5 kDa *Mycoplasma hyopneumoniae* antigen.

Similarly, it is possible within the spirit and scope of the present invention to employ a fragment or derivative of one or more of the hereinabove described antigens in producing an intranasally administered vaccine of the present invention in place of or in conjunction with one or more of such antigens. The term fragment of the antigen as used herein is a fragment of the antigen which includes an epitope which will produce an antibody which recognizes by such antigen. It is also possible that the fragment may immunoreact with serum of an animal (in particular swine) convalescing from mycoplasmal pneumonia.

The *Mycoplasma hyopneumoniae* antigens which are employed in the intranasally-administered vaccine may be obtained from *Mycoplasma hyopneumoniae* organisms and in particular from the membrane of *Mycoplasma hyopneumoniae* organisms. As hereinabove indicated, the *Mycoplasma hyopneumoniae* organisms and, in particular, the membrane of the *Mycoplasma hyopneumoniae* organism, contains both antigens which have immunosuppressive activity and antigens which do not have immunosuppressive activity. In obtaining antigens for the intranasally administered vaccine, it is necessary to recover selectively the *Mycoplasma hyopneumoniae* antigens which do not have immunosuppressive activity.

For example, a procedure for determining whether or not a compound or composition possesses immunosuppressive activity is reported in Suter, M., Kobisch, M. and J. Nicolet (1985). *Infect. and Immun.* Vol. 49, page 615. "Stimulation of immunoglobulin containing cells and isotype specific antibody response in experimental *Mycoplasma hyopneumoniae* infection in specific pathogen-free pigs".

In accordance with one method, the membrane of the *Mycoplasma hyopneumoniae* organism may be treated with a mild detergent, and in particular a non-ionic detergent to produce both a soluble and insoluble fraction Applicant has found that the insoluble fraction includes *Mycoplasma hyopneumoniae* antigens which lack immunosuppressive activity whereas the soluble fraction, obtained by treatment with a mild detergent, includes *Mycoplasma hyopneumoniae* antigens which lack immunosuppressive activity, as well as materials which have immunosuppressive activity. The insoluble fraction obtained by treating the membrane from *Mycoplasma hyopneumoniae* organism with a mild detergent may be employed for formulating an intranasally administered vaccine for protecting animals against mycoplasma pneumonia or, alternatively, the soluble fraction may be treated to remove materials which have immunosuppressive activity, whereby such fraction may be employed in formulating a vaccine.

The non-ionic detergent is employed in amounts which are sufficient to solubilize the *Mycoplasma hyopneumoniae* antigens which possess immunosuppressive activity, without solubilizing the *Mycoplasma hyopneumoniae* antigens which lack immunosuppressive activity. In general, the weight ratio of non-ionic detergent to *Mycoplasma hyopneumoniae* organism portion which is subjected to treatment is from 10 to 1 to about 0.05 to 1, and preferably from about 5.0 to 1 to 0.5 to 1. The treatment is generally effected at a temperature which does not exceed 40° C., with the temperature most generally being in the order of from 0° C. to 37° C.

The treatment is for a time sufficient to effect solubilization of the *Mycoplasma hyopneumoniae* antigens which possess immunosuppressive activity and in general, such time is in the order of from 0.5 to 12 hours; however, in some cases, longer or shorter times may be employed.

The solution employed to solubilize the antigen(s) generally has an ionic strength of from 0.05 to 1.0M salt. A preferred solubilizing agent contains 0.2M sodium ion.

As hereinabove indicated, in general, the membrane of the *Mycoplasma hyopneumoniae* organism is subject to such treatment. Such membrane may be obtained by disrupting the organism by procedures generally known in the art, such as a freeze-thaw cycle; sonication; etc. Alternatively, the antigen(s) may be derived from the whole organism. The selection of a suitable procedure is deemed to be within the scope of those skilled in the art from the teachings herein.

As a further alternative, the membrane derived from *Mycoplasma hyopneumoniae* organism may be treated with other agents to selectively solubilize the surface antigens which possess immunosuppressive activity and thereby provide an insoluble fraction containing *Mycoplasma hyopneumoniae* antigen(s) which lack immunosuppressive activity. As representative examples of other solubilizing agents, these may be mentioned: n-octylglucoside; sodium deoxycholate; CHAPS (3-[(3-Cholamidopropyl) dimethylammonio] 1-propane sulfonate, etc.

As another example of a procedure for obtaining *Mycoplasma hyopneumoniae* antigens which lack immunosuppressive activity, there may be mentioned electrophoretic procedures for separating the various *Mycoplasma hyopneumoniae* membrane antigens which lack immunosuppressive activity.

The above procedures and others should be apparent to those skilled in the art from the teachings herein.

In addition to obtaining *Mycoplasma hyopneumoniae* antigens and/or fragments thereof by treating *Mycoplasma hyopneumoniae* (*M.hyopneumoniae*) organisms, it is to be understood that the antigens and/or fragments thereof may be recombinant in origin and obtained by various methods of genetic engineering.

The recombinant *M.hyopneumoniae* antigens, for example, may be obtained through a recombinant DNA molecule or expression or cloning vehicle (vector or plasmid), which includes a DNA sequence which encodes at least one protein which is capable of eliciting an antibody which recognizes an epitope(s) of at least one *M.hyopneumoniae* antigen. The expression vehicle may be contained within a host organism transformed by such an expression vehicle.

More particularly the DNA sequence may encode at least one protein which is capable of eliciting an antibody which recognizes an epitope(s) of at least one of the following *M.hyopneumoniae* antigens: the 74.5, 36, or 41 kDa *M.hyopneumoniae* antigens.

The DNA sequence may encode a protein which is the entire antigen, or a fragment or derivative of the antigen or a fusion product of the antigen or fragment and another protein, provided that the protein which is produced from such DNA sequence is capable of eliciting an antibody which recognizes an epitope(s) of the *M.hyopneumoniae* antigen. Thus, for example, the DNA sequence may encode a protein which is a fragment of the 74.5 kDa antigen (a protein having a molecular weight of 43 kDa and which includes a portion of the 74.5 kDa antigen peptide sequence) provided that such fragment is capable of eliciting an antibody which recognizes an epitope(s) of the 74.5 kDa antigen.

Similarly, the DNA sequence may encode a protein which is a derivative of the antigen e.g.. a mutation of one or more amino acids in the peptide chain, as long as such derivative is capable of eliciting an antibody which recognizes an epitope(s) of a *M.hyopneumoniae* antigen as hereinabove described.

The DNA sequence may encode a protein which is a fusion product of (i) a protein which is capable of eliciting an antibody which recognizes an epitope(s) of the noted *M.hyopneumoniae* antigens and (ii) another protein.

As a result, the term "DNA sequence which encodes a protein which is capable of eliciting an antibody which recognizes an epitope(s) of the noted *M.hyopneumoniae* antigens" encompasses DNA sequences which encode for and/or express in appropriate transformed cells, proteins which may be the appropriate antigen, antigen fragment, antigen derivative or a fusion product of such antigen, antigen fragment or antigen derivative with another protein.

It is also to be understood that the DNA sequence present in the vector when introduced into a cell may express only a portion of the protein which is encoded by such DNA sequence, and such DNA sequence is within the noted terminology, provided that the protein portion expressed is capable of eliciting an antibody which recognizes an epitope(s) of one or more of the noted *M.hyopneumoniae* antigens. For example, the DNA sequence may encode the entire antigen; however, the expressed protein is a fragment of the antigen. It is also to be understood that the cloning vehicle may include DNA which encodes more than one *M.hyopneumoniae* antigen or fragment.

The appropriate DNA sequence may be included in any of a wide variety of vectors or plasmids. Such vectors include chromosomal, nonchromosomal and synthetic DNA sequences: e.g., derivatives of SV40; bacterial plasmids; phage DNA's; yeast plasmids; vectors derived from combinations of plasmids and phage DNAs, viral DNA such as vaccinia, adenovirus. fowl pox, virus, pseudorabies, etc.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art.

The DNA sequence in the vector is operatively linked to an appropriate expression control sequence(s) (promoter) to direct mRNA synthesis. As representative examples of such promoters, there may be mentioned: LTR or SV40 promoter, the *E. coli lac* or *trp*, the phage lambda PL promoter and other promoters known to control expression of genes in prokaryotic and eukaryotic cells or their viruses. The expression vector also contains a ribosome binding site for translation initiation and a transcription terminator. The vector may also include appropriate sequences for amplifying expression.

In addition, the expression vectors may contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein. Examples of host organisms and cells include *E. coli*, Salmonella organisms, Bacillus organisms, yeast cells and eukaryotic cells such as Bowes melanoma cells, Chinese hamster ovary cells, or insect cells. The selection of an appropriate host is deemed to be within the scope of those skilled in the art from the teachings herein.

As hereinabove indicated, the expression vehicle including the appropriate DNA sequence inserted at the selected site may include a DNA or gene sequence which is not part of the gene coding for the protein which is capable of eliciting antibodies which recognize epitopes of the noted *M.hyopneumoniae* antigen(s). For example, the desired DNA sequence may be fused in the same reading frame to a DNA sequence which aids in expression or improves purification or permits expression of the appropriate protein or increases the immunogenicity.

When seeking to develop a vaccine, neutralizing or protective antibodies could be targeted towards discontinuous, conformation-dependent epitopes of the native antigen. One must therefore consider whether the protein obtained from the recombinant expression system might have a three dimensional structure (conformation) which differs substantially from that of the original protein molecule in its natural environment. Thus, depending on the immunogenic properties of the isolated proteins, one might need to renature it to restore the appropriate molecular conformation. Numerous methods for renaturation of proteins can be found in the scientific literature and include; 1) denaturation (unfolding) of improperly folded proteins using agents such as alkali, chaotropic solvents, organic solvents, and ionic detergents followed by a renaturation step achieved by dilution, dialysis, or pH adjustment to remove the denaturant, and 2) reconstitution of proteins into a lipid bilayer or liposome to re-create a membrane like environment for the immunogenic protein.

As hereinabove noted, in some cases, even through the DNA sequence included in the cloning vehicle encodes for a specific antigen, the expressed protein may be only a fragment of such antigen. For example, in employing *E.coli* as a host organism, the codon TGA is a stop codon for *E.coli* whereby if the DNA sequence in the cloning vehicle includes the codon (TGA) for the amino acid tryptophan, such codon is interpreted in *E.coli* as a stop codon whereby the entire antigen may not be expressed.

In accordance with one embodiment, a cloning vehicle which is to be used for transforming an organism which recognizes the codon TGA as a stop codon (such as *E.coli*.) may include (in addition to the DNA sequence which encodes a desired *M.hyo.* protein having a TGA codon as part of the DNA sequence) an additional DNA sequence which encodes t-RNA which translates the stop codon in the host organism as an amino acid and inserts tryptophan into the *M.hyo.* protein chain which is produced in the transformed organism. For example, a DNA sequence which encodes the trpT176 gene may be inserted into the cloning vehicle with the DNA sequence having a TGA codon, which DNA sequence encodes a desired *M.hyopneumoniae* protein, and the use of such a cloning vehicle in *E. coli* expresses a desired *M.hyopneumoniae* protein which includes tryptophan. Thus, for example, as shown in Example 4, the 74.5 kDa *M.hyopneumoniae* antigen may be expressed in *E. coli* by transforming *E. coli* with a cloning vehicle which includes a DNA sequence which encodes the 74.5 kDa *M.hyo.* antigen and a DNA sequence which encodes the trpT176 gene. As shown in Example 2, transforming *E. coli* with a cloning vehicle which includes a DNA sequence which encodes the 74.5 kDa *M.hyopneumoniae* antigen and does not include a DNA sequence which encodes the trpT176 gene, expresses a fragment of the 74.5 kDa *M.hyopneumoniae* antigen.

Such expressed protein will be sometimes hereinafter referred to as a "recombinant *M.hyopneumoniae* antigen, "however, as hereinabove indicated, such protein may not correspond to a *M.hyopneumoniae* antigen in that it may also be a fragment, derivative or fusion product. The term "recombinant *M.hyopneumoniae* antigen" also encompasses such fragments, derivatives and fusion products. As in the case of the proteins, or *M.hyopneumoniae* antigens, obtained from *M.hyopneumoniae* organisms, the recombinant *M.hyopneumoniae* antigens described above also lack immunosuppressive activity.

It is also to be understood that other procedures for obtaining recombinant *M.hyopneumoniae* antigens may be employed as well. Thus, the scope of the present invention is not limited to the described embodiments for obtaining such antigens.

It is also to be understood that variants of *M.hyopneumoniae* antigens of recombinant and or other origins, may be employed as well. One such example of a recombinant variant, although the scope of the present invention is not to be limited thereby, is the r116 variant of the 74.5 kDa antigen, which may be expressed by *E. coli*, as hereinafter described.

Extensive sequence homology has been found between the 74.5 kDa antigen and the *E. coli* dnaK protein. Two differences in the amino termini which are noteworthy are that valine residues at positions 17 and 27 of the 74.5 kDa *M.hyopneumoniae* antigen significantly reduce the predicted T-cell recognition character of these regions of the antigen relative to the *E.coli* dnaK protein. Such protein domains are associated with the efficient presentation of the antigen to the immune system. By the use of site-directed mutagenesis, the valines at positions 17 and 27 may be replaced with cysteine and arginine, respectively. These two changes restore two regions of predicted amphipathic helicity present in the *E.coli* dnaK protein. A gene or genes for a derivative containing the two amino acid residue substitutions may be transferred into an *E. coli* expression vector. An example of such an expressed recombinant protein is known as the r116 variant of the 74.5 kDa *M.hyopneumoniae* antigen, as hereinafter described.

In accordance with another aspect of the present invention, there is provided a method for protecting an animal against mycoplasmal pneumonia which comprises adminstering intranasally to the animal a vaccine which comprises (a) one or more proteins, as hereinabove described, which elicit an antibody which recognizes a *Mycoplasma hyopneumoniae* antigen which lacks immunosuppressive activity: and/or (b) either (i) at least one nuclease or fragment or derivative thereof, which produces antibodies which recognize extrinsic nuclease of *Mycoplasma hyopneumoniae,* or (ii) an antibody or fragment or derivative thereof having paratope(s) which are recognized by an extrinsic nuclease of *M. hyopneumoniae.*

The extrinsic nuclease or fragment or derivative thereof, when employed, may be a DNase and/or RNase or derivative, thereof which elicits antibodies which recognize DNase and/or RNase secreted by and/or exosed on the surface of *Mycoplasma hyopneumoniae* organisms (extrinic DNase or extrinsic RNase).

When DNase is employed, the preferred DNase or fragment and/or derivative thereof is a DNA endonucleae.

An intranasally administered vaccine for protection against mycoplasmal pneumonia, and in particular for protecting swine against mycoplasmal pneumonia, is comprised of one or more proteins which elicits an antibody which recognizes a *Mycoplasma hyopneumoniae* antigen Which lacks immunosuppressive activity, or fragments or derivatives thereof, as hereinabove described, in combination with suitable agents that may enhance the immunogenic response. Examples of such agents comprise adjuvants and/or carriers, although in some cases, neither carrier nor adjuvant may be required to achieve an efficacious response. Selection of a suitable immunopotentiator is deemed to be within the scope of those skilled in the art from the teachings herein.

In general, the vaccine contains from about 1 microgram to about 2.000 micrograms per dose of said one or more proteins, preferably from about 10 micrograms to about 200 micrograms per dose.

If multiple doses are employed, in general, the vaccine would not be administered in an amount which exceeds 3 doses over a period of ten weeks.

The invention will now be described with respect to the following examples; however, the scope of the present invention is not to be limited thereby.

BRIEF DESCRIPTION OF THE DRAWINGS

FIG. 6 is the DNA sequence encoding the *M. Hyopneumoniae* 74.5 kDa antigen and the amino acid sequence of the protein encoded by such DNA sequence;

FIG. 7 is a DNA sequence and the amino acid sequence encoded thereby, said DNA sequence being inserted into the plasmid pUC18 to form pWHA148;
FIG. 14 is a DNA sequence encoding the *M. hyopneumoniae* 41 kDa antigen and the amino acid sequence of the protein encoded by such DNA sequence;
FIG. 17 is a schematic of the construction of the plasmid m13 MYCO107 from m13 MYCO102.

EXAMPLE 1

Extraction of *M.hyopneumoniae* Antigens

Figure 1:
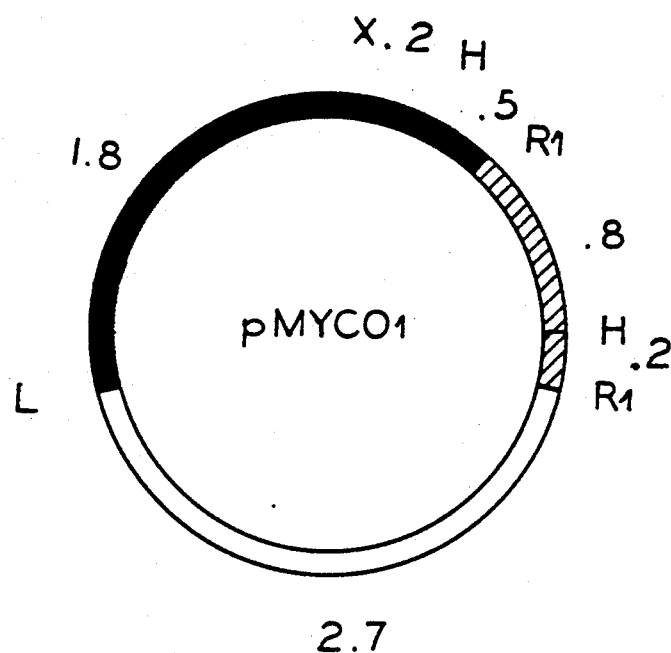
FIG. 1 is a diagram of the plasmid pMYCO1.

*Mycoplasma hyopneumoniae* is grown in Friis medium to a density of approximately $10^9$ to $10^{10}$ color changing units per milliliter. The cells are harvested by centrifugation and washed four times with phosphate buffered saline. The cells are lysed in 10 mM Tris 10 mM EDTA by repeated freeze thaw cycles in which the cells are transferred alternately between a dry-ice ethanol bath and a 37° C. bath with constant mixing. Insoluble components and unlysed cells are removed by high speed centrifugation. The membranes left in suspension are harvested by ultra-high speed centrifugation (33,000 g for 45 minutes), washed in phosphate buffered saline, and solubilized by Triton X-100 phosphate buffered saline solution. At this point, the Triton-soluble and Triton-insoluble components may be separated by ultra-high speed centrifugation (100.000 g for 45 minutes ). The Triton soluble fraction consists of many of the same proteins as the Triton-insoluble fraction.

The specific protective antigens in the insoluble fraction were identified by indirect enzyme-linked immunoassay. Proteins of *Mycoplasma hyopneumoniae* which make up the protective fraction were separated by SDS-polyacrylmide gel electrophoresis and transferred to a nitrocellulose sheet by blotting. Sera obtained from convalescent pigs were then incubated with the nitrocellulose sheets and the immunoreactive proteins recognized by biotinylated goat antisera prepared against pig antibodies. The recognized antigens were identified by their subsequent reaction with an avidin-biotin peroxidase conjugate which causes a color to develop at the bound protein.

The immuno-reactive proteins which make up the protective fraction were characterized as to their approximate molecular weights by SDS, 12% polyacrylamide-gel electrophoresis. They include: 22.5, one or more of 34, one or more of 36, 41, 44, 48, 52, 64, 68, 74.5, 79. 88.5, 96.5, and 121 kilo-Dalton components.

The 36 kDa component has a sequence of amino acid residues in its amino terminus of: $^1$Met-Ala-Asn-Ser-Asp-Lys-Ile-Ala-Leu-Asn-Asn-Ile-Gly-Ala The 41 kDa component has a sequence of amino acid residues in its amino terminus which consists of: 1 Met-Asp-Lys-Phe-Arg-Tyr-Val-Lys-Pro-Gly-Gln-Ile-Met--Ala-Lys-Asp-Glu-Glu-Met-Ile-Arg-Phe-Leu-Asp-Ile---Asp-Gly-Asn-Leu-Leu The 48 kDa component has a sequence of amino acid residues in its amino terminus which consists of: 1 Ala-Lys-Ile-Thr-Thr-Glu-Gly-Lys-Lys-Asp-Phe---Arg-Ser-Lys The 74.5 kDa component has a sequence of amino acid residues in its amino terminus which consists of: 1 Met-Ala-Lys-Glu-Ile-Ile-Leu-Gly-Ile-Asp-Leu-Gly-Thr-Thr-Asn-Ser-Val-Val-Ala-Ile-Ile-Glu-Asn-Gln-Lys-Pro---Val-Val-Leu

EXAMPLE 2

74.5 Kda M.hyopneumoniae Antigen and Expression of the Full Length Thereof in E. Coli

Preparation of M.hyopneumoniae DNA

Strain P-57223 (obtained from Dr. Charles Armstrong, Purdue University) was grown in 1 liter of Friis medium to a density of approximately $10^9$ to $10^{10}$ color changing units per ml. The cells were harvested by centrifugation and resuspended in 2 ml phosphate buffered saline which brought the total volume to 3.25 ml. The suspension was then mixed with a solution consisting of 24.53 g cesium chloride dissolved in 19.75 ml 10 mM Tris pH 8.0 1 mM EDTA and 1.53 of 10 mg/ml ethidium bromide was added. This was mixed with a solution consisting of 3.87 g cesium chloride dissolved in 2.15 ml 10 mM Tris pH 8.0. 1 mM EDTA, 8.9% Sarkosyl. The resulting suspension was incubated at 65° C. for 10 minutes to completely lyse the cells. The DNA was separated by equilibrium buoyant density centrifugation in a Sorvall TV850 rotor at 43.000 rpm for 18 hours, and withdrawn with an 18 gauge needle. This DNA was subjected to two additional buoyant density centrifugations in a Sorvall TV865 rotor at 55,000 rpm for 7 and 18 hours respectively, each time the band of genomic DNA being removed with an 18 gauge needle. The resulting DNA solution was extracted with cesium chloride saturated isopropanol, to remove ethidium bromide, and extensively dialyzed against 10 mM Tris pH 8.0, 1 mM EDTA. to remove the isopropanol and cesium chloride.

Preparation of Genomic Library

A preparative digest of 200 μg genomic DNA of Mycoplasma hyopneumoniae P-57223 (P-57223 obtained from Dr. C. Armstrong. Purdue University) was done using 200 units of EcoR1 in a total volume of 1 ml and 250 μl aliquots were removed at 6 min, 25 min. 42 min and 63 min.

The four preparative samples of partially digested Mycoplasma DNA then combined (200 μg) and loaded on to an exponential sucrose gradient. The gradient was centrifuged in a Sorvall AH627 rotor at 26 k rpm for 21 hrs at 15° C.

The gradient was then slowly fractioned from the bottom by collecting 15 drop fractions (90 fractions total) 20 μl of each fraction was then run on a 1% agarose gel as described above. Fractions containing DNA fragments smaller than 18 kbp and larger than 15 kbp were pooled (fractions 32–40) and dialyzed against TE (10 mM Tris.HCl pH 7.5. 1 mM EDTA pH8.0) to remove the sucrose. The DNA (3.5 ml) was then precipitated with ethanol and resuspended to about 15 μl (1 mg/ml) and stored at −20° C.

EcoR1 Arms of bacteriophage lambda-dash were obtained from Vector Cloning Systems (StrataGene) and were ligated at a concentration of 200 μg/ml to Mycoplasma target DNA at a concentration of 25 μg/ml in a total volume of 10 μusing T4 ligase (Boehringer GmbH) at a concentration of 100 units/ml. The ligation reaction was incubated at room temperature for 2 hours. 4 μl of the ligation was then packaged into lambda particles using the in vitro packaging kit Gigapack (StrataGene). The phage was then titered on E. coli strain P2392 (StrataGene) and found to be 7.75 × $10^5$ pfu/ml (3.1 × $10^5$ pfu/μg of lambda-dash).

Antiserum

1. Rabbit antiserum. A new Zealand White rabbit was immunized with approximately $10^{11}$ color changing units of M.hyopneumoniae strain J (ATCC) in complete Freund's adjuvant (Sigma, St Louis). A booster injection of the same antigen in incomplete Freund's adjuvant (Sigma) was administered two weeks after the first injection. Hyperimmune serum was shown to react with greater than thirty mycoplasma proteins by 1-D gel Western blot analysis and to react with two proteins of approximately 74.5 kDa by 2-D Western blot analysis.

2. Mouse antisera. Monospecific serum was prepared as described above with the exception that DBA/2 mice were immunized with approximately 10 μg of electrophoretically pure 74.5 kDa antigen from strain P-57223 followed by an equal dose booster immunization. The 74.5 kDa antigen is obtained as described in U.S. application Ser. No. 030.130, filed on Mar. 26. 1987. Hyperimmune sera was shown to react with a single mycoplasma 74.5 kDa protein band by 1-D Western Blot analysis and to react with two 74.5 kDa proteins by 2-D gel Western Blot analysis. The 74.5 kDa antigen was prepared as described in U.S. application Ser. No. 7/030,130 which is hereby incorporated by reference.

3. Pig antisera. Purdue mini-pigs were immunized with 100 μg of electrophoretically pure 74.5 kDa antigen in incomplete Freund's adjuvant (Sigma). An identical booster injection was administered two weeks after the first injection. Hyperimmune sera was shown to react with a single mycoplasma 74.5 kDa protein by both 1-D and 2-D gel Western blot analysis. This protein is identical to one of the two recognized by the hyperimmune mouse serum. These pigs were afforded a measure of protection from mycoplasma pneumonia by the vaccination.

Screening of Library

The library was screened with rabbit anti-M.hyopneumoniae (which immunologically recognizes the 74.5 kDa antigen, in addition to other mycoplasma surface proteins). Aproximately 200 recombinants were selected by the initial screen because they reacted immunologically with the rabbit anti-serum. These positives were subsequently screened with mouse anti-74.5 kDa, which was raised against electrophoretically purified antigen. Ten recombinants were selected because they produced material in E. coli which cross-reacted immunologically with the mono-specific serum.

Cloning the Gene for the 74.5 kDa Antigen

Based on a partial amino acid sequence of the 74.5 kDa antigen the oligonucleotide families shown in the figure below (COD 558 and COD 559) were synthesized. DNA from the 10 immuno-positive recombinants was

```
 1
Ala———Lys———Glu———Ile———Ile———Leu———Gly———Ile———Asp———Leu———
        AAA  GAA  ATA  ATA  TTG  GG
          G    G    C    C    C   A
                    T    T    T
                                   C
        COD 558

15
Ser———Val———Val———Leu———Ile———Asp———Glu———Asn———Gln———Lys———Pro
        GTG  CTG  ATA  GAC  GAA  AA
          A    T    C    T    G
          T         T
          C
                    COD 559
``` prepared, digested with EcoR1, analyzed by gel electrophoresis, and each shown to contain portions of the *M.hyopneumoniae* genome composed of several EcoR1 restriction fragments.

Both COD 558 and COD 559 were shown by Southern blot analysis to hybridize to a 7,800 base pair (7.8 kb) EcoR1 restriction fragment present in 6 of the 10 recombinants.

The hybridization conditions are as follows:
Hybridization:
6×NET
5×Denhardts
$2\times10^6$ cpm kinased probe
37° C.
18 hours
Wash:
6×NET
0.1% SDS
3×at room temperature
2×at 37° C.
6×NET:
1M NaCl
90 mM Tris pH 7.6
6 mM EDTA In order to subclone this fragment, one recombinant containing the 7.8 kb fragment (in addition to other adjacent fragments) was named lambda 5-5-59. its DNA was prepared and digested with EcoR1, ligated to EcoR1 digested pWHA148 and transformed into *E.coli* strain JM83. One transformant was named pMYCO16; its DNA was prepared and digested with a number of different restriction endonucleases in order to derive the restriction map shown in FIG. 5.

Plasmid pWHA148 is prepared by inserting synthetic oligonucleotides into the Hind III site of pUC18. The amino terminal coding sequence of the X-complementing peptide of B-galactosidase is shown in FIG. 7, and contains 8 additional restriction sites over the parent pUC18. The oligonucleotide insert into pUC18 is shown in FIG. 7 between the Sph1 and Hind III sites.

Both COD 558 and 559 were shown by Southern analysis to hybridize to the 0.6 kb AccI-AsuII restriction fragment of pMYCO16. DNA sequence analysis of the 0.6 kb fragment showed: 1) it included a region of homology to COD 558 and COD 559; and 2) all but 3 of the amino acids predicted by the fragment's DNA sequence matched the protein sequence determined for the 74.5 kDa as shown below.

Protein sequence: [1]———Ala Lys Glu Ile Ile Leu Gly Ile Asp
Clone sequence: met ala lys glu ile ile leu gly ile asp -continued Protein sequence: [11]Leu Gly Thr Val Asn Ser Val Val Leu Ile
Clone sequence: leu gly thr thr asn ser val val ala ile
Protein sequence: [21]Asp Glu Asn Gln Lys Pro Val Val Leu
Clone sequence: ile glu asn gln lys pro val val leu Subsequent re-analysis of the actual amino acid sequence indicated that the three mismatches could have been due to ambiguous amino acid identification.

On the restriction map of pMYCO16 (FIG. 5) the gene begins within the 0.6 kb AccI-AsuII restriction fragment, extends clockwise within the 0.3 kb AsuII-ClaI, and 1.3 kb ClaI- HindIII fragments, and ends short of the HindIII site.

The DNA-amino acid sequence of the 74.5 kDa gene is shown in FIG. 6.

Expression of Full Length *M.hyopneumoniae* 74.5 kDa Antigen in *E. Coli*

DNA from pMYCO16 was transformed into *E. coli* strain CY15000. One transformant was selected, grown in L-broth at 37° C. to an $OD_{550}=2$, and the cells harvested by centrifugation. The cells were washed free of contaminating medium components by resuspension in M9 buffer and harvested again by centrifugation. The resulting cell pellet was resuspended at one-fifteenth the original culture volume in a solution consisting of 0.5 mg/ml hen egg-white lysozyme dissolved in 25 mM Tris pH 8.0, 10 mM EDTA; incubated at 25° C. for 10 minutes; and sonicated at 4° C. for 15 seconds. A portion of the resulting lysate was subjected to polyacrylamide gel electrophoresis and a new 43 kDa protein was identified.

The pMYCO16 43 kDa expression product was shown to react by Western blot with the mouse antiserum raised against the 74.5 kDa *M.hyopneumoniae* antigen.

The pMYCO16 43 kDa expression product was shown to react by Western blot with the pig antisera raised against the 74.5 kDa *M.hyopneumoniae* antigen.

Partial Purification of the *E. Coli* Produced 74.5 Antigen Fragment

One *E. coli* strain CY15000 transformant was selected grown in one liter of L-broth at 37° C. to an $OD_{550}=2$, and the cells harvested by centrifugation. The cells were washed free of contaminating medium components by resuspension in M9 buffer and harvested again by centrifugation. The resulting cell pellet was resuspended in 20 ml of a solution consisting of 0.5 mg/ml hen egg-white lysozyme dissolved in 25 mM Tris pH 8.0, 10 mM EDTA; incubated at 25° C. for 10 minutes; separated into two aliquots; and each sonicated at 0° C. for 60 seconds. The resulting lysate was cleared of insoluble debris by centrifugation at 13,000×g for 10 minutes at 4° C. Sufficient ammonium sulfate (4.52 g) was added to bring the supernatant to 40% saturation and the insoluble protein was removed by centrifugation. Sufficient ammonium sulfate (1.2 g) was subsequently added to bring the 40% supernatant up to 50% saturation and the insoluble protein was harvested by centrifugation subjected to polyacrylamide gel electrophoresis, and shown by Western blot analysis (using miniature pig serum prepared as described above) to contain the 43 kDa pMYCO16 expression product. The enriched antigen fraction was dialysed against PBS prior to its use as a vaccine.

EXAMPLE 3

41 kDa *M. hyopneumoniae* Antigen

EcoR1 Arms of bacteriophage lambda-dash were obtained from Vector Cloning Systems (StrataGene) and were ligated at a concentration of 200 μg/ml to Mycoplasma target DNA prepared as in Example 1 at a concentration of 25 μg/ml in a total volume of 10 μl using T4 ligase (BMB) at a concentration of 100 units/ml. The ligation reaction was incubated at room temperature for 2 hours. Four μl of the ligation was then packaged into lambda particles using the in vitro packaging kit Gigapack obtained from StrataGene. The phage was then titered on *E. coli* strain P2392 (StrataGene) and found to be 7.75×10$^5$ pfu/ml (3.1×10$^5$ pfu/μg of lambda-dash).

Construction of Mixed Oligonucleotide Probes

All possible DNA sequences that could encode a known partial amino acid sequence of the 41 kDa *M.hyopneumoniae* antigen were determined. Two 17 bp sequences were identified. Two mixed sequence oligonucleotide probes were synthesized as Cod 447 and Cod 455.

0.2% SDS
0.1 mg/ml sonicated salmon sperm DNA
250 μg/ml *E. coli* tRNA
Prehybridization was done at 37° C. for 2½ hours.

The pre-hybridization solution was then drained from the bags and 3 ml of a second pre-hybridization solution was added to each bag. The second prehybridization solution was identical to the first except that 1 ml of 100 mg/ml lambda gt11 DNA and 5 ml of 362 μg/ml *E. coli* DNA was added per 50 ml. Both DNAs were sonicated to less than 500 bp, boiled 10 min and quick chilled immediately prior to use. The filters were allowed to pre-hybridize in this solution for 2½ hours at 37° C.

Probes were kinased as follows: 2.4 ul of COD 447 (2.0 OD/ml) using 18.5 μl $^{32}$p-ATP (7000 Ci/mMole) or 6 5 μl of COD 455 (2.0 OD/ml) using 49.0 μl $^{32}$p-ATP (7000 Ci/mMole) in an 80 ul reaction mix with 20 units of T$_4$ kinase (Boehringer)

Each kinased probe was added to 10 ml prehybridization solution. The bags were drained of prehybridization solution and hybridization solution containing the probe was added to approximately 2 ml/filter. These were allowed to incubate overnight (approximately 16 hours) at 37° C.

The filters were then washed 4×10 min in 1 liter 6×SSC at room temperature followed by 4×10 min in 100 ml 3M Tetramethylammonium chloride, 50 mM Tris-HCl, pH8.0, 2 mM EDTA. 1 mg/ml SDS (TMAC) (DNA, 82, 1585-1588) at room temp. The filters were then washed at 50° C. for 10 min in 400 ml TMAC. The filters were then wrapped in saran wrap (without first drying the filters) and exposed to Kodak XAR5 film overnight with double intensifying screens at −80° C. Appropriate plaques showing hybridization to both COD 455 and COD 447 were picked and DNA was prepared. The DNA was digested with EcoR1 and electrophoresed on two 1% agarose gels. The gels were then Southern blotted. The Southern blots were hybridized to either COD 447 or COD 455 as described above. These blots showed that two of the phage contain a 2.5 kbp EcoR1 fragment which hybridized to both COD 447 and COD 455. These phages were named lambda Myco 1 and lambda Myco 2.

—Cys—Tyr—Val—Lys—Pro—Gly—Gln—Ile—Met—Ala—Lys—Cys—

```
       Cod 455                         Cod 447
         G                G                       G
    T    T    T    A       T      A     T         G
    TGC  TAC  GTA  AAG  CGA  GG  CAG  ATC  ATG  GCA  AAA  TG
              C        C              A      C        G
```

Screening Library for the 41 k Dalton Antigen Gene

The library of Example 1 was plated on *E. coli* strain LE392 at a density of ∼2000 pfu/135 mM-petri plate on 5 plates and grown overnight at 37° C. Two nitrocellulose filters were lifted off of each plate and processed according to W. D. Benton and R. W. Davis (*Science:* 196 180, 1977). The dried filters were rewetted in 0.9M NaCl, 90 mM Tris-HCl, pH 7.5. 6 mM EDTA. The filters were then placed into bags and 2.5 ml pre-hybridization solution filter was added.

The prehybridization/hybridization solution contained:
6×NET
5×Denhardt's
0.1 mM rATP
1.0 mM NaPPi
10.0 mM Sodium Phosphate pH 7.5

Large scale DNA preps of lambda Myco 1 and lambda Myco 2 were done according to Yamamoto, K. R. et al., *Virology* 40: 734, 1970. DNA from lambda Myco 1 was digested with EcoR1, ligated to EcoR1 digested vector pUC9. and transformed into *E. coli* strain JM83. One transformant was named pMYCO1 (FIG. 1); its DNA was prepared and digested with a number of different restriction endonucleases in order to derive the restriction map shown in FIG. 1. By comparison of restriction maps for lambda Myco 1 and pMYCO1 it was found that the additional 1.0 kb EcoR1 fragment of mycoplasma DNA in pMYCO1 is not actually adjacent to the 2.5 kb EcoR1 fragment in the genome.

Figure 2:
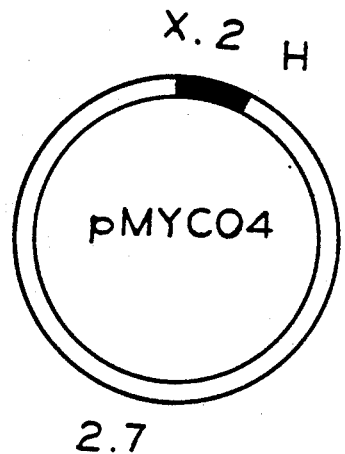
FIG. 2 is a diagram of the plasmid pMYCO4.

Both COD 455 and COD 447 were shown by Southern blot analysis to hybridize to the 0.2 kb XhoI-HindIII restriction fragment of pMYCO1. In order to subclone the 0.2 kb XhoII-HindIII fragment for DNA sequence analysis, DNA from pMYCO1 was digested with XhoI and HindIII, the 0.2 kb fragment purified, ligated to the XhoI and HindIII digested vector pWHA148, and transformed into *E. coli* strain JM83. One transformant was named pMYCO4 (FIG. 2); its DNA was prepared and digested with XhoI and HindIII in order to derive the restriction map shown in FIG. 2.

DNA sequence analysis of the 0.2 kb fragment showed: 1) it included a region of homology to COD 455 and COD 447 and 2) all but three of the amino acids predicted by the DNA sequence matched the protein sequence determined for the 41 kDa antigen as shown below.

Protein
sequence: [1]Met Asp Lys Phe Cys Tyr Val Lys Pro Gly
Clone
sequence: met asp lys phe arg tyr val lys pro gly
Protein
sequence: [11]Gln Ile Met Ala Lys Cys Glu———Ile/Met Ile
Clone
sequence: gln ile met ala lys asp glu glu met ile
Protein
sequence: [21]————Phe Leu———Ile————Ile Asn Leu Leu
Clone
sequence: arg phe leu asp ile asp gly asn leu leu Subsequent re-analysis of the actual amino acid sequence indicated that the three mismatches could have been due to ambiguous amino acid identification.

Figure 3:
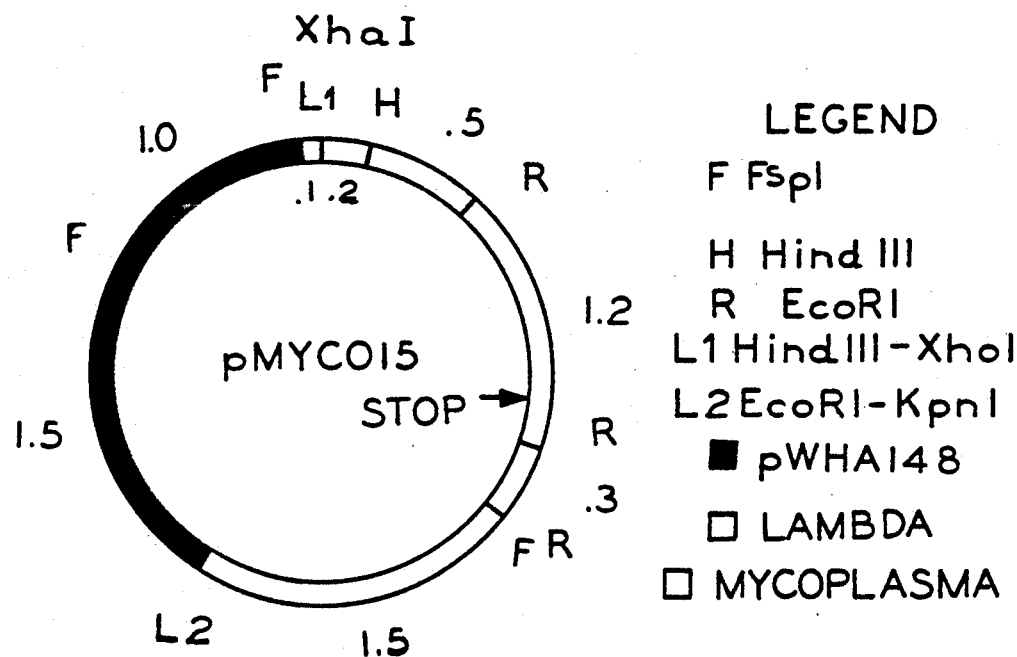
FIG. 3 is a diagram of the plasmid pMYCO15.

Analysis of a partial restriction map of lambda Myco 1 (not shown) indicated that the 0.2 kb XhoI-HindIII fragment was located approximately 1.5 kb distant from one of the mycoplasma DNA-lambda vector junctions. In order to clone the entire gene, lambda Myco 1 DNA was digested with XhoI and KpnI, ligated to XhoI and KpnI digested vector pWHA148, and transformed into *E. coli* strain JM83. One transformant was named pMYCO15 (FIG. 3); its DNA was prepared and digested with several different restriction enzymes in order to generate the restriction map shown in FIG. 3.

DNA sequence analysis of the mycoplasma DNA portion of pMYCO15 showed that the insert includes the complete 41 kDa antigen gene. On the restriction map of pMYCO15 the gene begins within the 0.2 kb XhoI-HindIII fragment extends clockwise within the 0.5 kb HindIII - EcoR1 and 1.2 kb EcoRI fragments, and ends 0.8 kb short of the EcoRI site. The amino acid sequence derived from the gene's DNA sequence is shown in FIG. 14.

Expression of *M.hyopneumoniae* 41 kDA Antigen Gene in *E. Coli*

Figure 4:
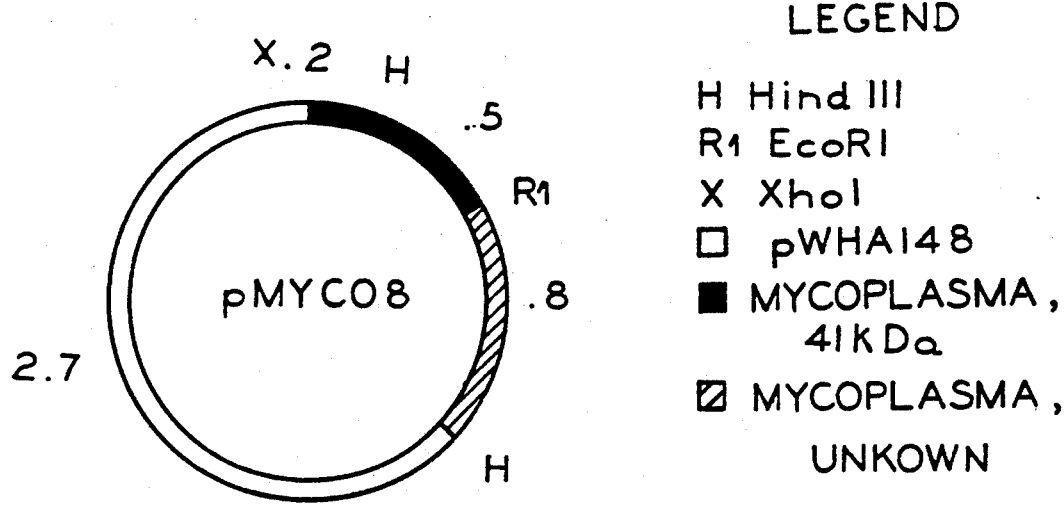
FIG. 4 is a diagram of the plasmid pMYCO8.

The DNA sequence of the 41 kDa antigen indicated that there were 14 TGA codons within the coding sequence. It is known that TGA codons identify the amino acid tryptophan in mycoplasma but normally terminate protein chain elongation in *E. coli*, therefore expression of the 41 kDa antigen in *E. coli* would normally result in the expression of the peptide encoded by the gene up to the first TGA encoded tryptophan. In order to increase expression of this fragment of the 41 kDA antigen. pMYCO1 (FIG. 1) was digested with HindIII, the 1.3 kb HindIII fragment purified and ligated to HindIII digested pMYCO4 (FIG. 2) and transformed into *E. coli* strain JM83. One transformant was named pMCYO8 (FIG. 4); its DNA was prepared and digested with several enzymes in order to derive the restriction map shown in FIG. 4.

The 41 kDa initiation methionine, located within the 0.2 kB XhoI - HindIII fragment, is approximately 0.2 kb distant from the lac promoter located in pWHA148. The TGA stop codon lies within the 0.5 kb HindIII - EcoR1 fragment.

DNA from pMYCO8 was transformed into *E. coli* strain W3110. One transformant was selected, grown in L-broth at 37° C. to an $OD_{550}=2$, and the cells harvested by centrifugation. The cells were washed free of contaminating medium components by resuspension in M9 buffer and harvested again by centrifugation. The resulting cell pellet was resuspended at one-fifteenth the original culture volume in a solution consisting of 0.5 mg/ml hen egg-white lysozyme dissolved in 25 mM Tris pH 8.0, 10 mM EDTA; incubated at 25° C. for 10 minutes; and sonicated at 4° C. for 15 seconds. A portion of the resulting lysate was subjected to polyacrylamide gel electrophoresis and a new 14 kDa protein was identified. This protein has the expected molecular weight of a fragment of the 41 kDA antigen comprised of the peptide encoded by the gene up to the first TGA codon.

DBA/2 mice were immunized with 20 micrograms of electrophoretically pure 41 kDa antigen (isolated from *M.hyopneumoniae* in complete Freund's adjuvant (Sigma). A booster injection was administered in incomplete Freund's adjuvant (Sigma) 2 weeks after the initial injection and the mice were bled 1 week later. By Western blot analysis of total *M.hyopneumoniae* proteins, the antiserum was shown to react at a 1:100 dilution specifically with the 41 kDa antigen. The pMYCO8 14 kDa expression product was shown to react by Western blot with the mouse antiserum raised against the 41 kDa *M.hyopneumoniae* antigen.

EXAMPLE 4

Figure 5:
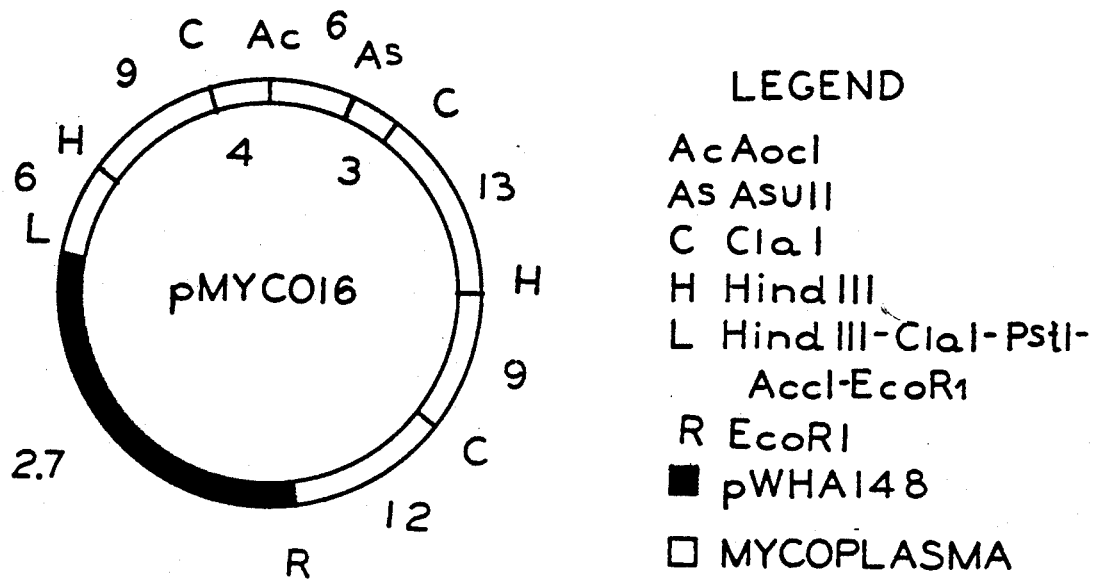
FIG. 5 is a diagram of the plasmid pMYCO16.
Figure 8:
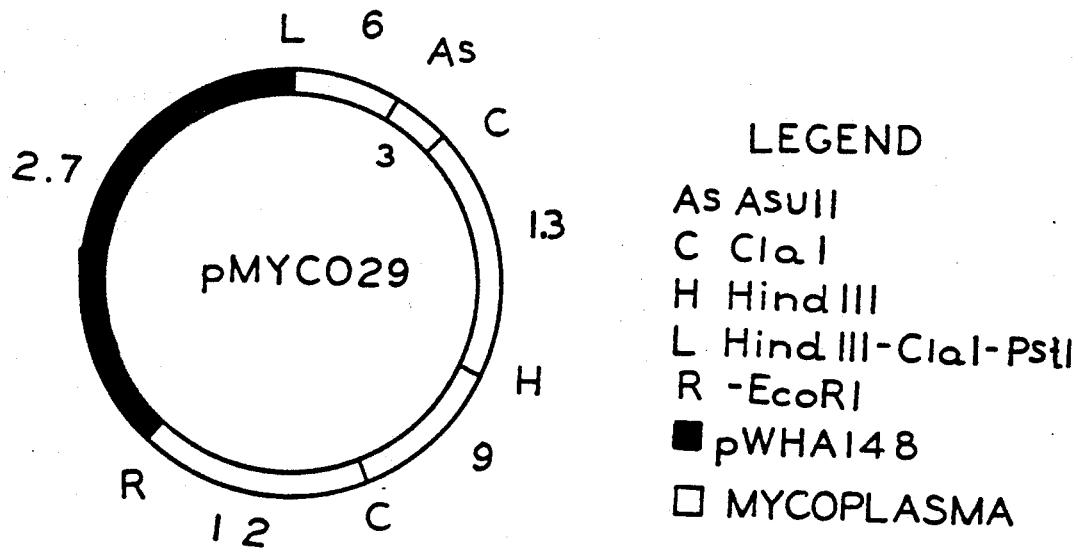
FIG. 8 is a diagram of the plasmid pMYCO29.

Expression of full length *M.hyopneumoniae*, 74.5 kDa antigen in *E. Coli* pMYCO16 DNA (FIG. 5) was digested with AccI, treated with Mung Bean nuclease to remove the single stranded AccI tails. re-ligated to delete the 1.9 kb AccI fragment in front of the 74.5 kDa antigen gene and transformed into *E.coli* strain JM83. One transformant was named pMYCO29; its DNA was digested with a number of different restriction endonucleases in order to derive the restriction map shown in FIG. 8.

pMYCO29 was subjected to DNA sequence analysis which showed that a spontaneous deletion had occured at the ligation juncture where two bases were deleted and the PstI site was retained, as shown below (only a portion of the 5'to 3' strands are represented).

pMYCO29 expected:
TTGCATGCCTGCAGGTACTTTCTTTTGTCT
PstI pMYCO29 observed:
TTGCATGCCTGCAGGCTTTCTTTTGTCT
PstI Construction of pMYCO31 and Expression of 74.5 kDa Antigen Fragment Because the mycoplasma insert of pMYCO29 is oriented away from the Lac promoter of pWHA148, it was desired to insert the gene into another expression vector, pUC9. The two base deletion enabled the gene for the 74.5 kDa antigen to be placed in the same reading frame as the beta-galactosidase gene of *E. coli* vector pUC9.

Figure 9:
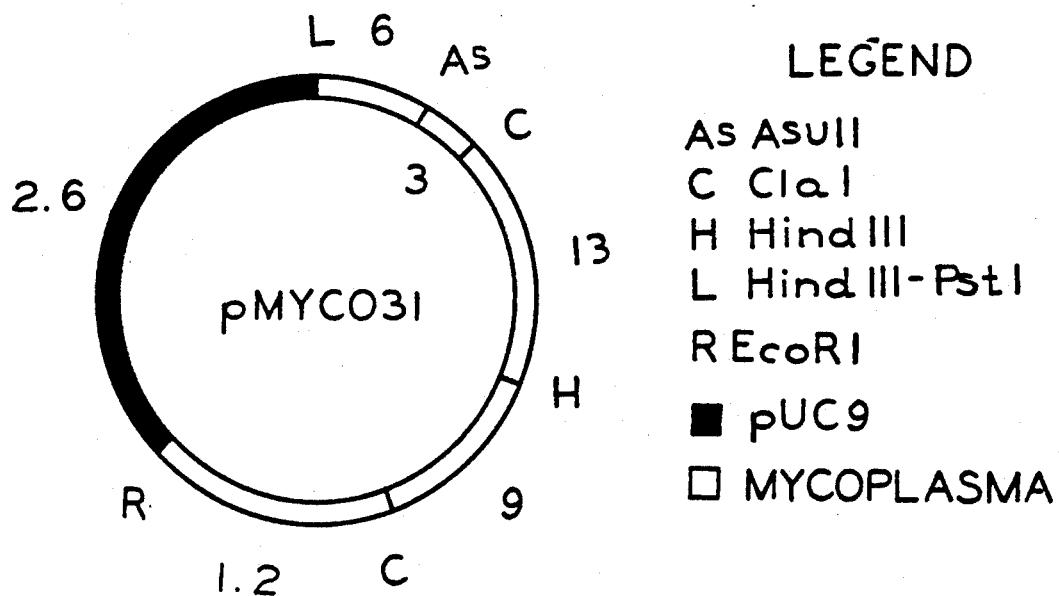
FIG. 9 is a diagram of the plasmid pMYCO31.

In order to perform this construction, pMYCO29 DNA was digested with PstI and EcoR1, the PstI-EcoR1 fragment containing the entire 74.5 kDa coding sequence was purified, ligated to the PstI and EcoR1 digested vector pUC9, and transformed into *E. coli* strain JM83. One transformant was named pMYCO31 (FIG. 9): its DNA was prepared and transformed into *E. coli* strain CY15000 by the transformation procedure described above.

Construction of pMYCO32

Figure 10:
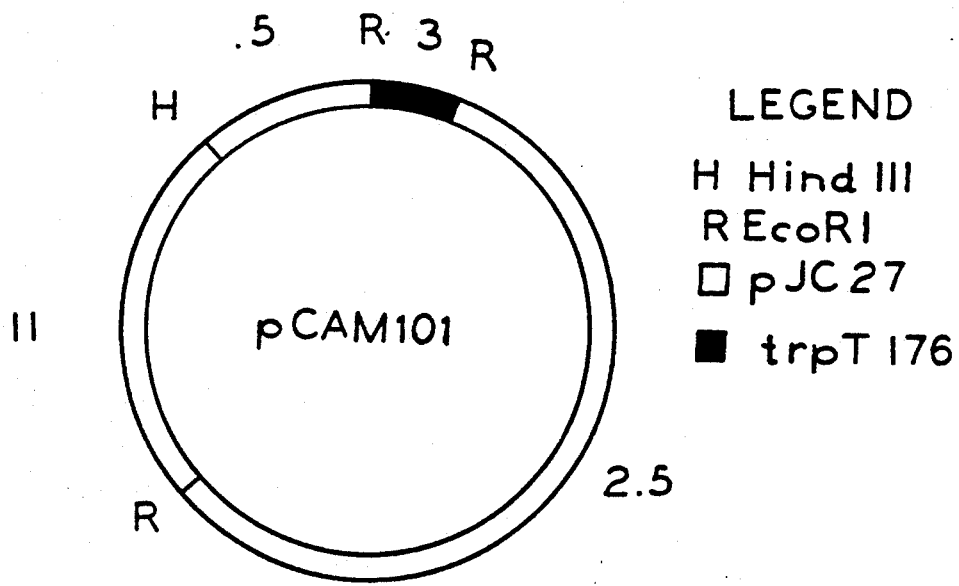
FIG. 10 is a diagram of the plasmid pCAM101.
Figure 11:
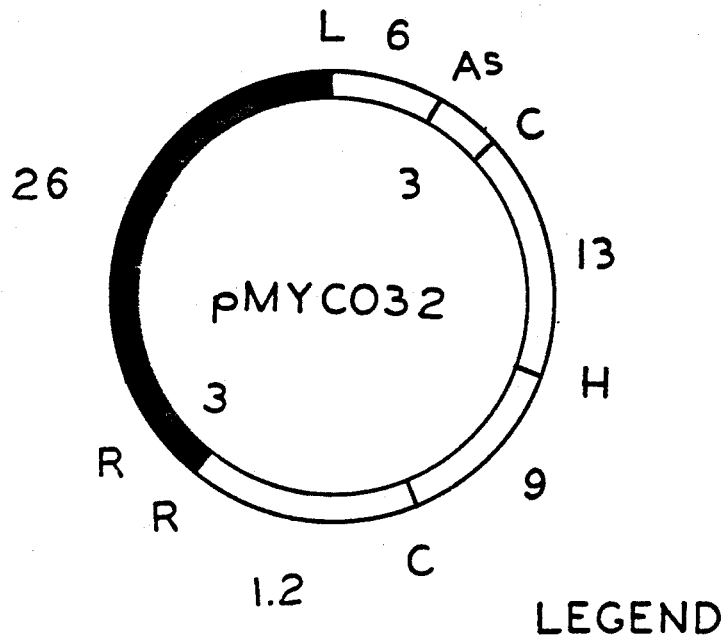
FIG. 11 is a diagram of the plasmid pMYCO32.
Figure 12:
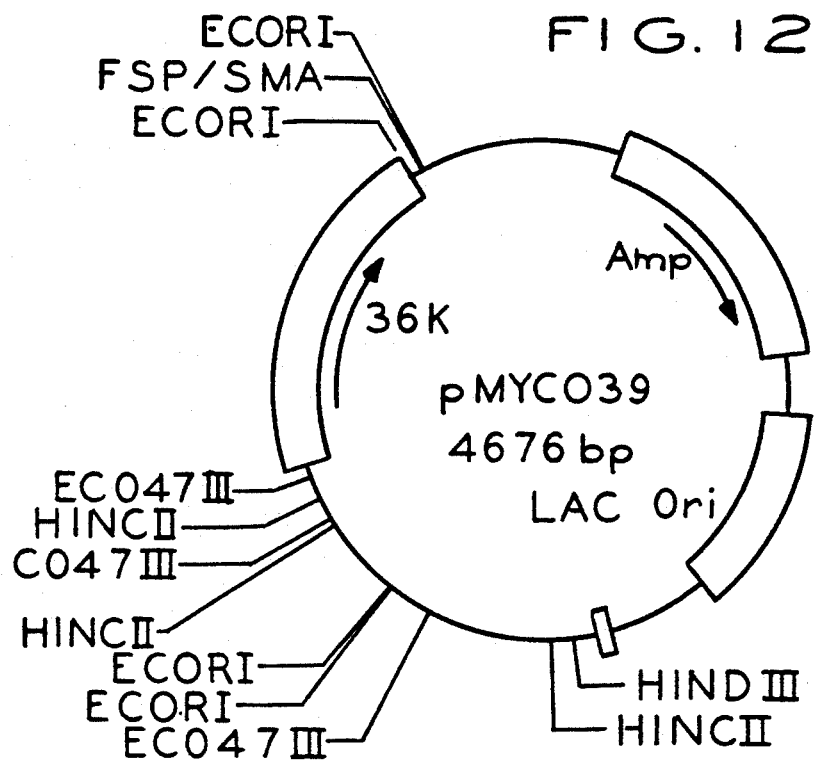
FIG. 12 is a diagram of the plasmid pMYCO39.
Figure 13:
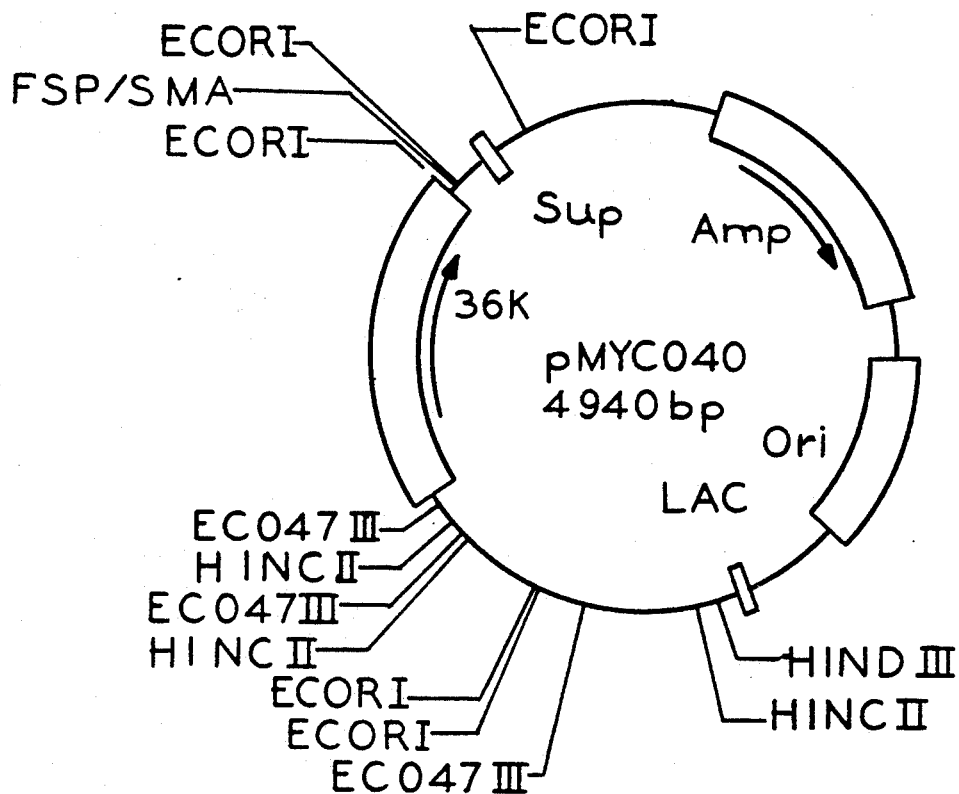
FIG. 13 is a diagram of the plasmid pMYCO40.
Figure 15:
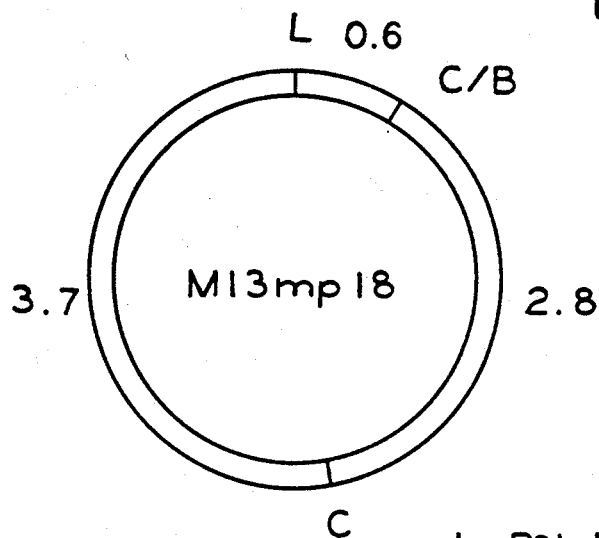
FIG. 15 is a diagram of the plasmid M13mp18.
Figure 16:
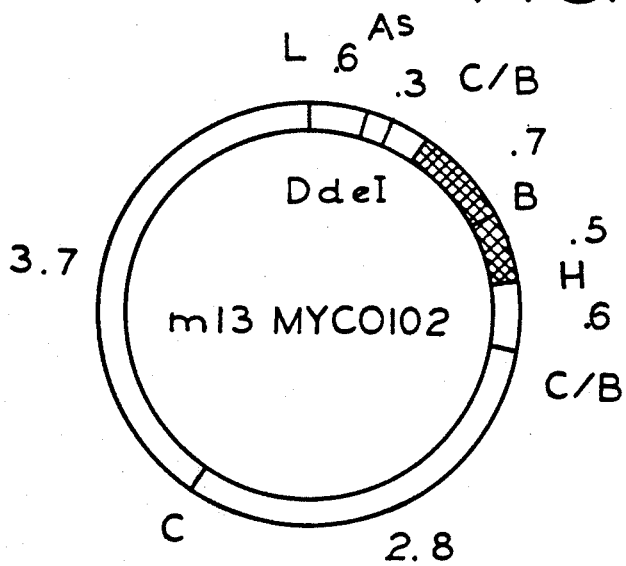
FIG. 16 is a diagram of the plasmid m13 MYCO102.
Figure 18:
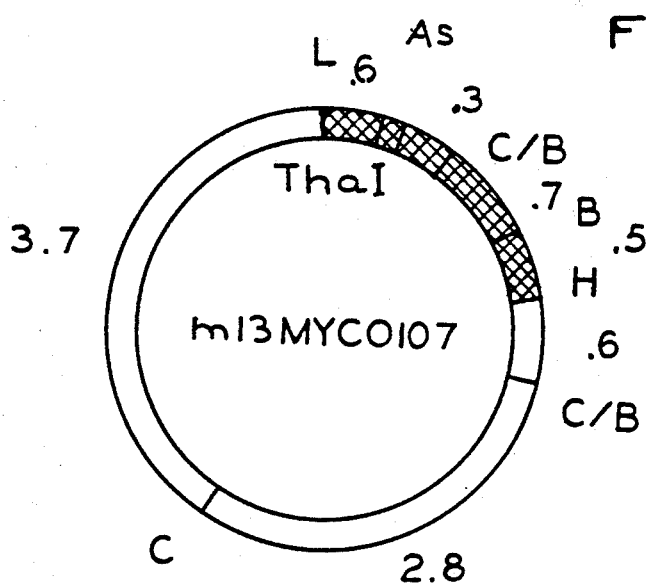
FIG. 18 is a diagram of the plasmid m13 MYCO107.
Figure 19:
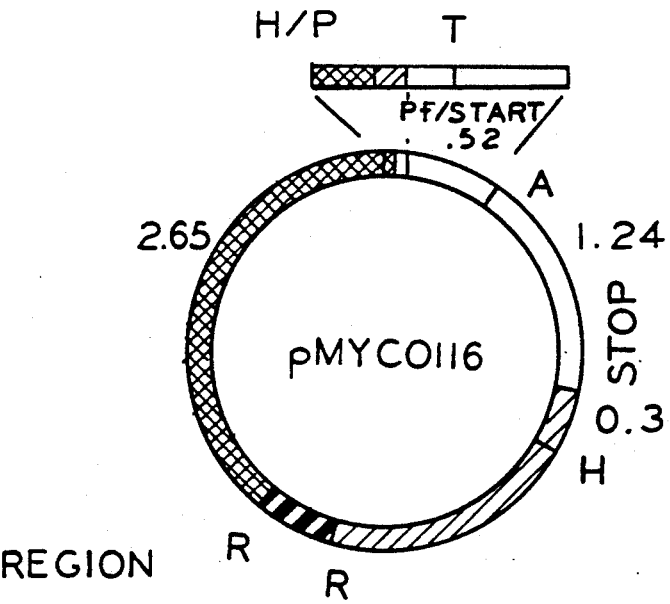
FIG. 19 is a diagram of the plasmid pMYCO116.

Plasmid pCAM101 was obtained from James Curran located at University of Colorado, Boulder, Colo. as a convenient source of the trpT176 gene and is shown in FIG. 10. DNA from pCAM101 was digested with EcoR1, the 0.3 kb EcoR1 fragment which contains the trpT176 gene was purified, ligated to EcoR1 digested pMYCO31, and transformed into *E. coli* strain CY15000. One transformant was named pMYCO32 and its restriction map is shown in FIG. 11.

Expression of *M.hyopneumoniae* 74.5 kDa Antigen in *E. Coli*

A CY15000 (pMYCO32) transformant was selected, grown in L-broth, a lysate prepared as previously described, and a portion subjected to polyacrylamide gel electrophoresis. New 75 kDa and 43 kDa proteins were identified by gel electrophoresis which protein was shown by Western blot to react with the previously described pig antisera raised against the 74.5 kDa M.hyopneumoniae antigen.

EXAMPLE 5

*Expression of r*116 Variant of *M.hyopneumoniae* 74.5 kDa Antigen in *E. coli Construction of M*13MYCO102

Plasmid pMYCO31 was used as the source of the 74.5 kDa antigen's gene (see Example 4, FIG. 9). M13mp 18 RF DNA (Bethesda Research Labs), a 7253 base pair phage vector (FIG. 15). was digested with HindIII (Boehringer Mannheim) and PstI (Bethesda Research Labs), ligated with T4 ligase (Boehringer Mannheim) to HindIII, PstI digested pMYCO31 and transformed into *E.coli strain* JM103. The DNA from one transformant. M13MYCO102, was digested with restriction endonucleases in order to derive the restriction map shown in FIG. 16.

Construction of M13MYCO107

Based on the DNA sequence of the 74.5 kDa antigen gene, a 96 base long synthetic oligonucleotide, COD 639 (see below) was designed to alter

```
11LEU—GLY—THR—THR—ASN—SER—VAL—VAL—ALA—ILE—ILE—GLU

CTT—GGA—ACA—ACA—AAC—TCA—GTT—GTT—GCA—ATT—ATT—GAA
      —TGT—TGT—TTG—AGT—ACA—CAA—CGT—TAA—TAA—CTT

23ASN—GLN—LYS—PRO—VAL—VAL—LEU—GLU—ASN—PRO—ASN—GLY

AAT—CAA—AAA—CCT—GTC—GTT—CTC—GAA—AAT—CCC—AAC—GGA
TTA—GTT—TTT—GGA—GCG—CAA—GAG—CTT—TT

COD 639
``` two amino acids in the antigen's N-terminus through site directed mutagensis based on the methods of Taylor et al. (1985) Nucl. Acid Res. 13: 8749–8764 and Taylor et al. (1985) Nucl. Acid Res. 13:8764–8785. The mutagenesis with COD 639 changes $Val^{17}$ to $Cys^{17}$, destroying a DdeI site, and changes $Val^{27}$ to $Arg^{27}$, creating a ThaI site. These changes restore two regions of predicted amphipathic helicity present in the *E.coli* dnaK protein as hereinabove described.

Single strand DNA of M13MYCO102, prepared according to Nakamaye. K. and F. Eckstein (1986) Nucl. Acid. Res. 14:9679–9698, was used as the template in the steps shown in FIG. 17 used to generate the recombinant candidate named M13MYCO107; its DNA was prepared and digested with ThaI in order to verify one of the expected mutational changes. As predicted. M13MYCO107 (FIG. 18) has an additional ThaI site which converts a 2 kb fragment into two fragments of 0.4 and 1.6 kb. DNA sequence analysis of M13MYCO107 compared to M13MYCO102 confirmed both changes and indicated that no other changes took place within 70 base paris on either side of COD 639.

Construction of pMYCO116

Purified pMYCO32 DNA (see Example 4, FIG. 11) was digested with PflmI. (New England Biolabs), phosphatased with Calf Intestine Phosphatase (CIP: Boehringer Mannheim), digested with PstI (Promega Biotech) and AsuII (New York Biolabs), and phosphatased with CIP again, ligated to PstI, AsuII digested M13MYCO107 with T4 ligase (Boehringer Mannheim), and transformed into *E.coli* strain JM83. One transformant was named pMYCO116, its DNA purified and digested with HindIII in order to verify a 2.2 kb insert site. Purified pMYCO116 DNA (see FIG. 19) was used to transform E.coli strain CY15000. A purified colony was grown in L-Broth containing 100 μg per ml ampicillin. The cells were harvested by brief centrifugation, resuspended in 8% sucrose, 0.5% Triton X-100, 50 mM EDTA, 10 mM Tris pH8.3 and 0.66 mg/ml hen egg white lysozyme (HEL: Sigma) then heated to 100° C. briefly. Plasmid DNA from the supernatant was digested with HindIII to verify the presence of the proper insert. ThaI and DdeI digests verified the presence of the new ThaI site and the lack of a DdeI site, converting two fragments of 0.26 and 0.76 kb into a single 1.0 kb fragment.

Expression of pMYCO116 Product

Cells of CY15000 (pMYCO116) were harvested. washed, sonicated for 15 seconds in 25 mM Tris pH 8.0, 10 mM EDTA. and 0.5 mg/ml hen egg white lysozyme and centrifuted 10 minutes. Two microliters of the supernatant (soluible fraction) was electrophoresed on a 12% polyacrylamide gel. pMYCO116 produced a 74.5 kDa protein, which comprised approximately 10% of the soluble protein, equivalent in size to that produced by pMYCO32.

Soluble fraction from a 125 ml culture was prepared as described and the 74.5 kDa product was electrophoretically purified. Amino acid sequence analysis of 31 amino terminal residues confirmed the engineered protein and was consistent with Val[17] being changed to Cys[17]. However, cysteine is not directly verifiable by protein sequence analysis due to its weak signal The change Val[27] to Arg[27] was confirmed by detection of arginine instead of valine at residue 27.

EXAMPLE 6

Preparation and Administration of Vaccine Purification of pMYCO32 Product for Use in a Vaccine

*E. coli* CY15000 (pMYCO32) was grown in potassium phosphate buffered minimal medium in a 14 liter Chemap fermenter to a cell density of 84 O.D.600.360 g (wet weight) of cells were harvested from 4.2 liters. 100 g of cells were suspended in 300 ml PBS containing 12 mM EDTA. Cell disruption was accomplished with a Menton-Gaulin homogenizer operating at 5–8,000 psi feed pressure. Up to ten moles EDTA is added per liter harvest material to aid homogenization. The homogenized material is then clarifeid by microfiltration. 50 ml of filtrate was applied to a 100 ml radial flow DEAE column where both the sample and the column were equilibrated with 50 mM NaPO$_4$, pH 7.0, 2 mM EDTA and the unbound fraction retained as product. This material is sterile filtered. Immediately prior to use. 100 $\mu$g./ml PBS may be emulsified for use as a vaccine. A unit dose is equivalent to 100 $\mu$g of the purified product.

Purification of pMYCO116 Product for Use in a Vaccine

*E.coli* CY15000 (pMYCO116) was grown in potassium phosphate buffered minimal medium in a 14 liter Chemap fermenter to a cell density of 84 O.D.$_{600}$· 360 g (wet weight) of cells were harvested from 4.2 liters. 100 g of cells were suspended in 300 ml PBS containing 12 mM EDTA and 0.5 mg/ml hen egg white lysozyme, incubated at 25° C. for 15 minutes, sonicated on ice for 2 minutes in 30 second bursts, and centrifuged at 13,000 g for 10 minutes at 4° C. The soluble fraction was retained. Polyacrylamide gel electrophoresis indicated the 74.5 kDa antigen comprised approximately 10% of the soluble fraction or approximately 2.5 g product per liter of fermentation culture. 50 ml of soluble fraction was applied to a 100 ml radial flow DEAE column where both the sample and the column were equilibrated with 50 mM NaPO$_4$, pH7.0, 2 mM EDTA and the unbound fraction retained as a product. Immediately prior to use, 100 $\mu$g product/ml PBS may be emulsified for use as a vaccine. A unit dose is equivalent to 100 $\mu$g of the purified product.

Six vaccine preparations were formulated for administration to six groups of piglets. For purposes of explanation of the following vaccines, r74.5 kDa is the 74.5 kDa antigen of *M. Hyopneumoniae* formed by a recombinant method, and r116 is a genetically engineered variant of the 74.5 kDa protein, in which two amino acid changes, as hereinabove described, in the 74.5 kDa antigen were made. All recombinant 74.5 kDa antigen preparations used antigen that was at least 95% pure. Amphigen is an oil-in-water adjuvant developed by MRKS Marketing Services, Inc., Elkhorn. Nebr. Alhydrogel is 3% Al(OH)$_3$. Quil A is a semipurified glycoside obtained from a crude extract of the bark from the tree *Quillaja saporaria*. The glycoside is capable of binding membrane proteins. Vaccines A, B. C, and D were formulated by Norden Laboratories and contained 100 ppm merthiolate. Vaccines E and F were formulated by CODON (South San Francisco, Calif.).

Vaccines A, B, C, D, and E were administered subcutaneously in the hip using ·2 ml per injection in an amount of 100 $\mu$g of antigen per pig per injection. Booster injections were given in the alternate hip.

Vaccine F was administered intranasally in an amount of 1.0 ml in each nostril for a total of 100 $\mu$g of antigen per pig per vaccination. The vaccine preparations are as follows:

VACCINES

A) PBS=Amphigen (control)
B) r74.5 kDA=Alhydrogel (12% by weight)
C) r74.5 kDA=Liposomes/Quil A
D) r74.5 kDA=Amphigen (5% v/v)
E) r116=Amphigen (5% v/v)
F) r74.5 kDA=PBS Forty-two piglets were divided into six groups of 7 swine. Each of the six groups (Groups A through F) was vaccinated with one of vaccines A, B, C, D, E, or F, respectively. The piglets were allotted to each group at 14 days of age. At this time all pigs were bled (3 ml). weighed, and vaccinated with 2 ml of one of Vaccines A, B, C, D, E or F, according to the group to which each piglet was assigned.

The piglets were weaned at age 28 days, and then vaccinated a second time at age 35 days. Prior to the second vaccination, all piglets were bled (3 ml).

When the piglets reached age 42 days, each piglet was placed in an isolation room which was cleaned and disinfected prior to the entry of the piglets. At age 49 days, all piglets are bled and weighed, and then given an intratracheal inoculation of 2 ml of $10^8$ CCU of strain P-5722-3 *M.hyopneumoniae*.

The piglets are again bled and weighed when 63 and 77 days old. At 77 days, all pigs are immobilized with 1.4 to 2.3 mg/kg of Surital, and then electrocuted, and exsanguinated. The lungs are removed from all piglets and scored for lesions. Weight gain data for each piglet at pre-challenge and necropsy are also collected. Lung Lesion Scores and Weight Gain data are listed in Tables 1 and 2 below, respectively.

TABLE 1

| Pig No. | Lung Lesion Scores (percent) | | |
|---|---|---|---|
| | Consolidated | Mottled | Total |
| Group A - PBS + Amphigen (control) | | | |
| 1 | 16.2 | 24.7 | 40.9 |
| 2 | 3.0 | 43.6 | 46.5 |
| 3 | 38.4 | 6.5 | 44.9 |
| 4 | 2.8 | 38.9 | 41.7 |
| 5 | 7.2 | 25.5 | 32.7 |
| 6 | 8.4 | 0.0 | 8.4 |
| 7 | 5.2 | 0.0 | 5.2 |
| Mean | 11.6 +/− 12.7 | 19.9 +/− 18.0 | 31.5 +/− 17.4 |
| Group B - r74.5kDa + Alhydrogel | | | |
| 1 | 7.3 | 9.9 | 17.2 |
| 2 | 3.7 | 30.5 | 34.2 |
| 3 | 10.2 | 0.0 | 10.2 |
| 4 | 25.3 | 0.0 | 25.3 |
| 5 | 14.6 | 0.0 | 14.6 |
| 6 | 0.0 | 0.0 | 0.0 |
| 7 | 0.0 | 3.4 | 3.4 |
| Mean | 8.7 +/− 9.1 | 6.3 +/− 11.3 | 15.0 +/− 12.0 |
| Group C - r74.5kDa + Liposomes/Quil A | | | |
| 1 | 1.0 | 39.2 | 40.2 |
| 2 | 5.6 | 22.4 | 28.0 |
| 3 | 0.0 | 2.7 | 2.7 |

TABLE 1-continued

| | Lung Lesion Scores (percent) | | |
|---|---|---|---|
| Pig No. | Consolidated | Mottled | Total |
| 4 | 11.3 | 0.0 | 11.3 |
| 5 | 3.2 | 0.0 | 3.2 |
| 6 | 5.4 | 0.0 | 5.4 |
| 7 | 11.3 | 3.1 | 14.4 |
| Mean | 5.4 +/− 4.6 | 9.6 +/− 15.3 | 15.0 +/− 14.2 |
| Group D - r74.5kDa + Amphigen | | | |
| 1 | 11.3 | 38.7 | 50.0 |
| 2 | 0.7 | 31.2 | 31.9 |
| 3 | 21.0 | 14.3 | 35.3 |
| 4 | 0.6 | 14.3 | 14.9 |
| 5 | 13.3 | 14.4 | 27.7 |
| 6 | 1.2 | 9.7 | 10.9 |
| 7 | 18.1 | 7.2 | 25.3 |
| Mean | 9.5 +/− 8.6 | 18.5 +/− 11.7 | 28.0 +/− 13.0 |
| Group E - r116 + Amphigen | | | |
| 1 | 0.2 | 33.2 | 33.4 |
| 2 | 30.0 | 0.0 | 30.0 |
| 3 | 6.0 | 19.9 | 25.9 |
| 4 | 3.2 | 28.4 | 31.6 |
| 5 | 4.9 | 2.1 | 7.0 |
| 6 | 7.2 | 8.2 | 15.4 |
| 7 | 1.8 | 0.0 | 1.8 |
| Mean | 7.6 +/− 10.2 | 13.1 +/− 14.0 | 20.7 +/− 12.7 |
| Group F - r74.5kDa + PBS (Intransal) | | | |
| 1 | 4.0 | 18.0 | 22.0 |
| 2 | 3.8 | 0.0 | 3.8 |
| 3 | 0.0 | 0.0 | 0.0 |
| 4 | 2.7 | 0.0 | 2.7 |
| 5 | 6.1 | 0.0 | 6.1 |
| 6 | 6.4 | 0.0 | 6.4 |
| 7 | 3.5 | 0.0 | 3.5 |
| Mean | 3.8 +/− 2.2 | 2.6 +/− 6.8 | 6.4 +/− 7.2 |

TABLE 2

| | Weight Gain - Prechallenge to Necropsy | | |
|---|---|---|---|
| Pig No. | Prechallenge | Necropsy | Gain |
| Group A - PBS + Amphigen (control) | | | |
| 1 | 38 | 64 | 26 |
| 2 | 39 | 72 | 33 |
| 3 | 23 | 43 | 20 |
| 4 | 29 | 56 | 27 |
| 5 | 34 | 65 | 31 |
| 6 | 33 | 60 | 27 |
| 7 | 33 | 64 | 31 |
| Mean | 27.6 +/− 4.3 | | |
| Group B - r74.5kDa + Alhydrogel | | | |
| 1 | 39 | 69 | 30 |
| 2 | 40 | 74 | 34 |
| 3 | 24 | 54 | 30 |
| 4 | 22 | 48 | 26 |
| 5 | 26 | 52 | 26 |
| 6 | 29 | 48 | 19 |
| 7 | 37 | 71 | 34 |
| Mean | 28.4 +/− 5.3 | | |
| Group C - r74.5kDa + Liposomes/Quil A | | | |
| 1 | 32 | 60 | 28 |
| 2 | 33 | 58 | 25 |
| 3 | 18 | 42 | 24 |
| 4 | 21 | 48 | 27 |
| 5 | 28 | 56 | 28 |
| 6 | 27 | 57 | 30 |
| 7 | 30 | 52 | 22 |
| Mean | 26.3 +/− 2.8 | | |
| Group D - r74.5kDa + Amphigen | | | |
| 1 | 40 | 79 | 39 |
| 2 | 41 | 70 | 29 |
| 3 | 15 | 32 | 17 |
| 4 | 24 | 53 | 29 |
| 5 | 39 | 68 | 29 |
| 6 | 33 | 69 | 36 |
| 7 | 33 | 72 | 39 |
| Mean | 31.1 +/− 7.8 | | |
| Group E - r116 + Amphigen | | | |
| 1 | 35 | 66 | 31 |
| 2 | 22 | 46 | 24 |
| 3 | 21 | 40 | 19 |
| 4 | 26 | 60 | 34 |
| 5 | 37 | 69 | 32 |

TABLE 2-continued

| | Weight Gain - Prechallenge to Necropsy | | |
|---|---|---|---|
| Pig No. | Prechallenge | Necropsy | Gain |
| 6 | 32 | 64 | 32 |
| 7 | 36 | 69 | 33 |
| Mean | 29.3 +/− 5.6 | | |
| Group F - r74.5kDa + PBS (Intranasal) | | | |
| 1 | 32 | 61 | 29 |
| 2 | 25 | 53 | 28 |
| 3 | 19 | 45 | 26 |
| 4 | 15 | 31 | 16 |
| 5 | 33 | 66 | 33 |
| 6 | 30 | 59 | 29 |
| 7 | 33 | 64 | 31 |
| Mean | 27.4 +/− 5.7 | | |

The above results indicate a decrease in lung lesion scores in the group of piglets which were administered the recombinant 74.5 kDa antigen intranasally, as compared with the groups which received no M.hyopneumoniae antigen, or received subcutaneous injections of M.hyooneumoniae antigen.

It is to be understood, however, that the scope of the present invention is not to be limited to the specific embodiments described above. The invention may be practiced other than as particularly described and still be within the scope of the accompanying claims.

What is claimed is:

1. A method of protecting an animal against mycoplasmal pneumonia caused by Mycoplasma hyopneumoniae, comprising:
   administering intranasally to the animal a vaccine comprising at least one protein which elicits an antibody which recognizes a Mycoplasma hyopneumoniae antigen which lacks immunosuppressive activity, said vaccine including said at least one protein in an amount effective for protection against mycoplasmal pneumonia caused by Mycoplasma hyopneumoniae, said vaccine being essentially free of Mycoplasma hyopneumoniae antigens which have immunosuppressive activity.

2. The method of claim 1 wherein said at least one protein elicits an antibody which recognizes a Mycoplasma hyopneumoniae antigen which has a molecular weight of at least 10 kDA and no greater than 350 kDa.

3. The method of claim 2 wherein said at least one protein elicits an antibody which recognizes at least one of the 22.5 kDa, 34 kDa, 36 kDa, 41 kDa, 48 kDa, 52 kDa, 64 kDA, 74.5 kDa, 79 kDa, 88.5 kDa, 96 kDa, or 121 kDa Mycoplasma hyopneumoniae antigens.

4. The method of claim 3 wherein said at least one protein is a protein which elicits an antibody recognizes the 74.5 kDa Mycoplasma hyopneumoniae antigen.

5. The method of claim 1 wherein said at least one protein is the 22.5 kDA, 34 kDA, 36 kDA, 41 kDa, 48 kDa, 52 kDA, 64 kDa, 74.5 kDA, 88.5 kDa, 96.5 kDa, or 121 kDA Mycoplasma hyopneumoniae antigen.

6. The method of claim 5 wherein said at least one protein is the 74.5 kDa Mycoplasma hyopneumoniae antigen.

7. The method of claim 5 wherein the 74.5 kDa M.hyopneumoniae antigen is produced from M.hyopneumoniae organisms.

8. The method of claim 6 wherein said 74.5 kDa M.hyopneumoniae antigen is of recombinant origin.

9. The method of claim 8 wherein said recombinant 74.5 kDa M.hyopneumoniae antigen is encoded by a DNA sequence which encodes for at least a portion of the 74.5 kDa antigen having the amino acid sequence of FIG. 6.

10. The method of claim 9 wherein said DNA sequence includes mutations which change amino acid residue $Val^{17}$ to $Cys^{17}$ and change amino acid residue $Val^{27}$ to $Arg^{27}$ of said at least a portion of said 74.5 kDa antigen having the amino acid sequence of FIG. 6.